(12) United States Patent
Kim et al.

(10) Patent No.: US 9,696,306 B2
(45) Date of Patent: Jul. 4, 2017

(54) METHODS OF REDUCING LEVELS OF TAU

(71) Applicant: The Trustees of Columbia University in the City of New York, New York, NY (US)

(72) Inventors: Tae-Wan Kim, East Brunswick, NJ (US); Laura Beth Johnson McIntire, Long Island City, NY (US); Natalie Landman, New York, NY (US); Gina Finan, Brooklyn, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 127 days.

(21) Appl. No.: 14/020,776

(22) Filed: Sep. 6, 2013

(65) Prior Publication Data
US 2014/0171380 A1    Jun. 19, 2014

Related U.S. Application Data

(63) Continuation of application No. PCT/US2012/028345, filed on Mar. 8, 2012.

(60) Provisional application No. 61/450,615, filed on Mar. 8, 2011.

(51) Int. Cl.
| | |
|---|---|
| *A61K 31/137* | (2006.01) |
| *A61K 31/03* | (2006.01) |
| *A61K 31/085* | (2006.01) |
| *G01N 33/569* | (2006.01) |
| *C12N 5/0793* | (2010.01) |
| *G01N 33/50* | (2006.01) |
| *A61K 31/01* | (2006.01) |
| *A61K 31/145* | (2006.01) |
| *A61K 31/15* | (2006.01) |
| *A61K 31/41* | (2006.01) |
| *A61K 31/473* | (2006.01) |
| *A61K 31/5375* | (2006.01) |
| *A61K 31/7048* | (2006.01) |

(52) U.S. Cl.
CPC ....... *G01N 33/56966* (2013.01); *A61K 31/01* (2013.01); *A61K 31/03* (2013.01); *A61K 31/085* (2013.01); *A61K 31/137* (2013.01); *A61K 31/145* (2013.01); *A61K 31/15* (2013.01); *A61K 31/41* (2013.01); *A61K 31/473* (2013.01); *A61K 31/5375* (2013.01); *A61K 31/7048* (2013.01); *C12N 5/0619* (2013.01); *G01N 33/5058* (2013.01); *C12N 2501/385* (2013.01); *C12N 2506/02* (2013.01); *C12N 2533/50* (2013.01); *C12N 2533/52* (2013.01); *G01N 2800/2821* (2013.01)

(58) Field of Classification Search
None
See application file for complete search history.

(56) References Cited

U.S. PATENT DOCUMENTS

2005/0245617 A1* 11/2005 Meyerson et al. ... A31K 31/137
514/649

OTHER PUBLICATIONS

Jackowski, British Journal of Neurosurgery 9 (1995): 303-317.*

* cited by examiner

*Primary Examiner* — Robert C Hayes
(74) *Attorney, Agent, or Firm* — Baker Botts L.L.P.

(57) ABSTRACT

Successful CNS drug discovery requires a scalable, highly physiological neuronal model. Using directed differentiation of mouse embryonic stem (mES) cells, including mES cells isolated from a mouse model of Alzheimer's disease (AD), a highly homogeneous primary neuronal model amenable to phenotypic assays for production and synaptotoxicity of amyloid β-peptide was developed. This model furnishes a highly physiological and AD-relevant platform suitable for high throughput small molecule and functional genetic screens, providing specific small molecule compounds identified by such screens.

2 Claims, 18 Drawing Sheets

Figures 1D, 1E:
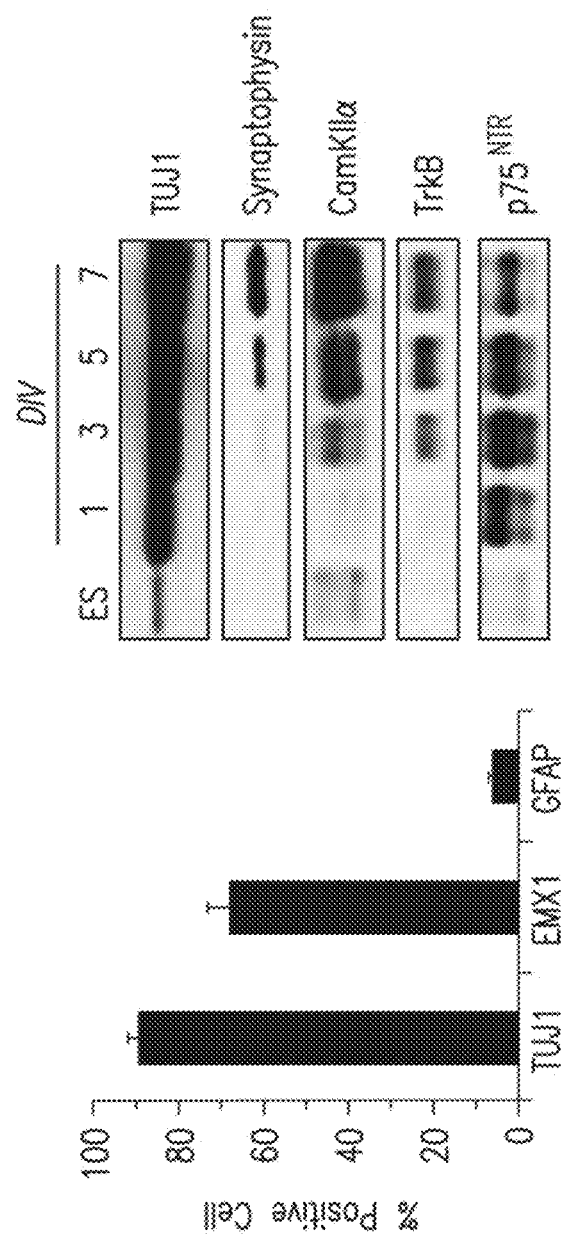

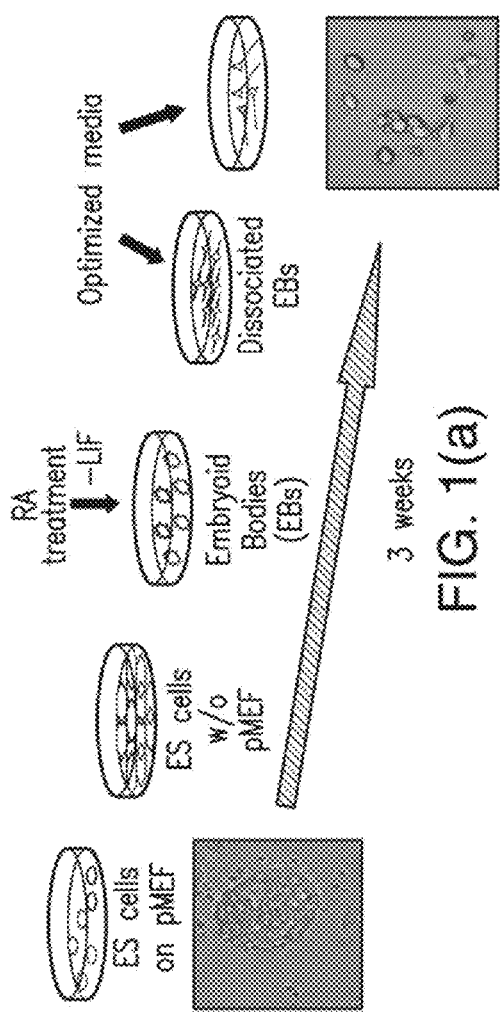
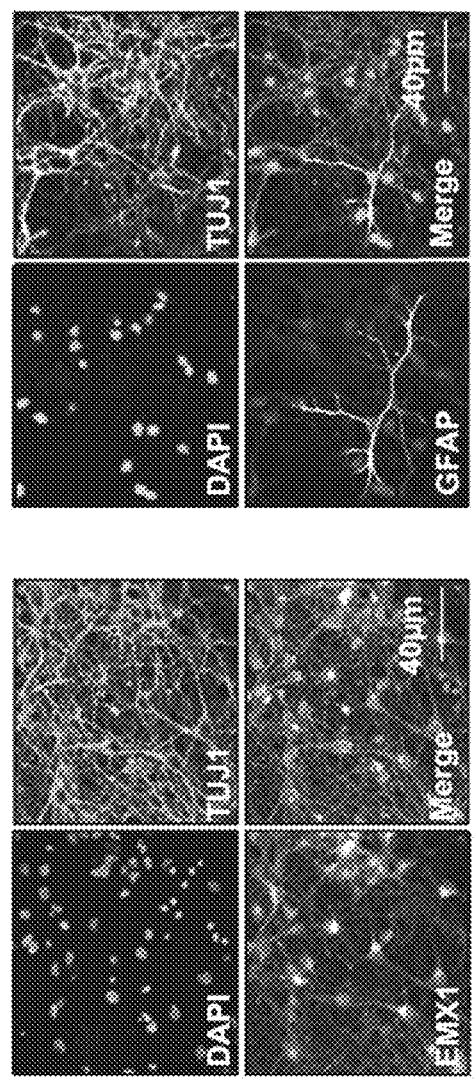
FIG. 1(a)
FIG. 1(b)
FIG. 1(c)

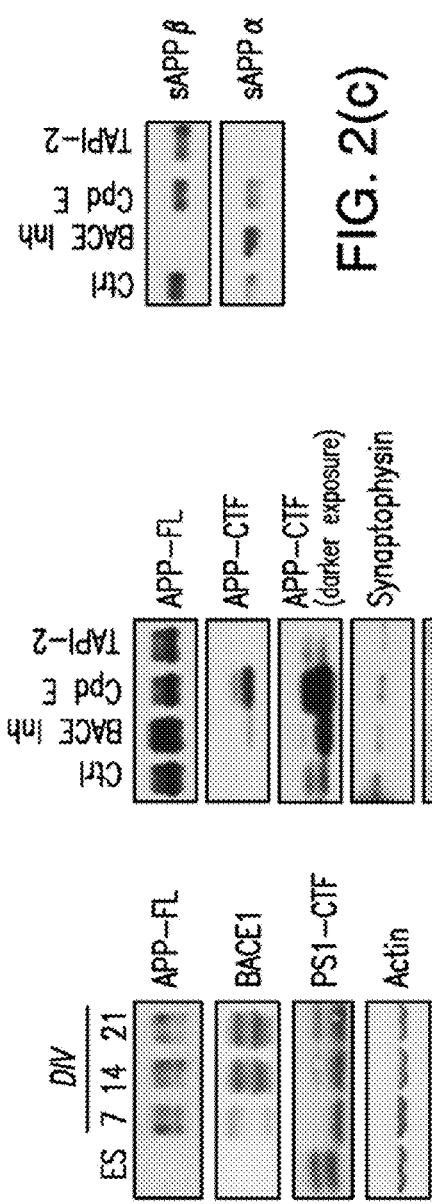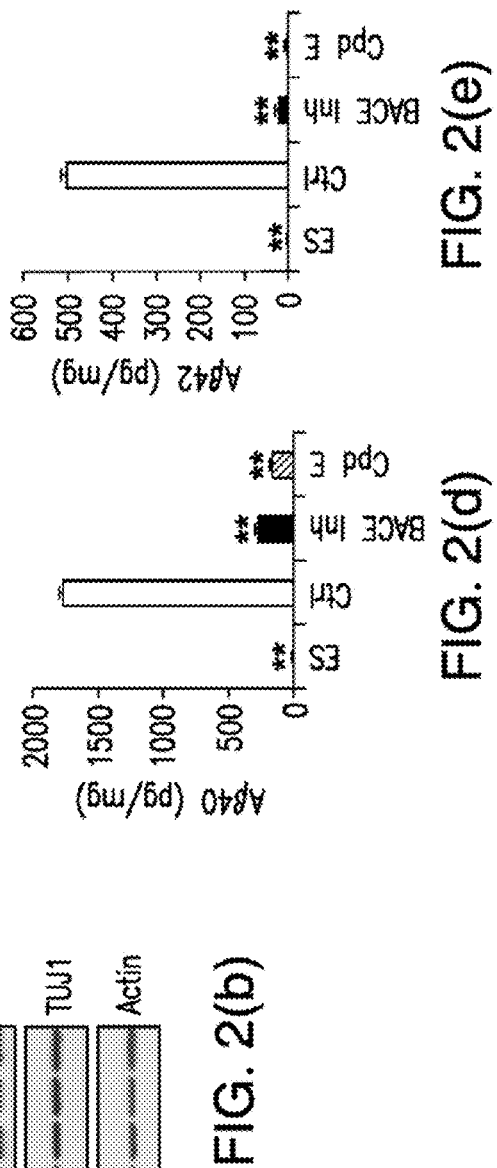

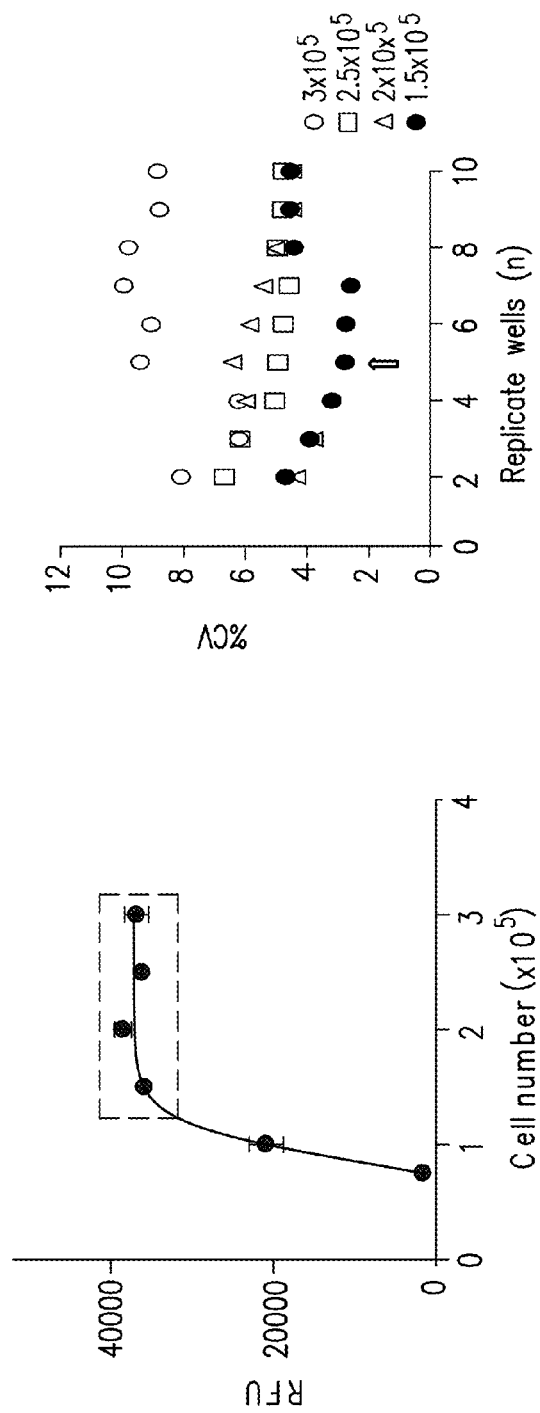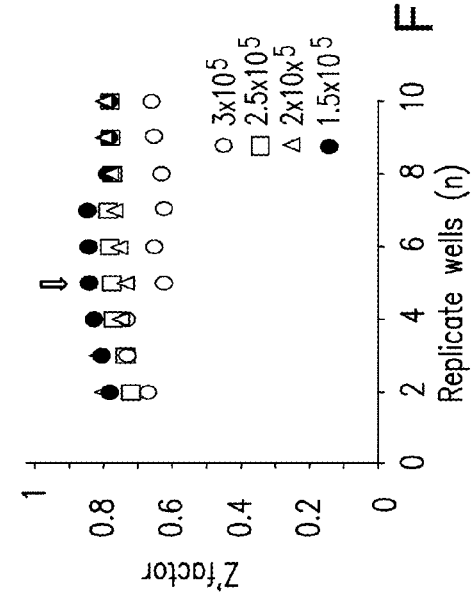
FIG. 2(f)  FIG. 2(g)  FIG. 2(h)

■ Control (n=11)
□ Aβ (n=12)

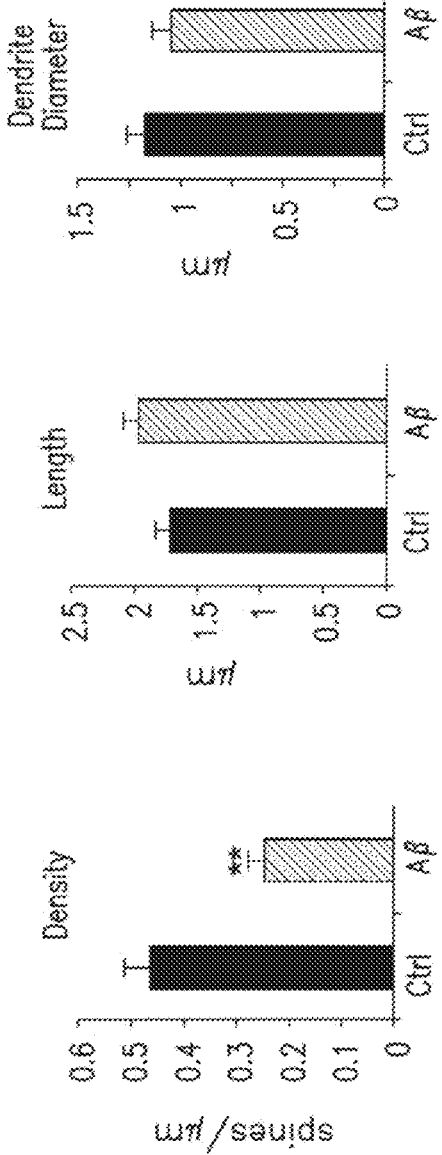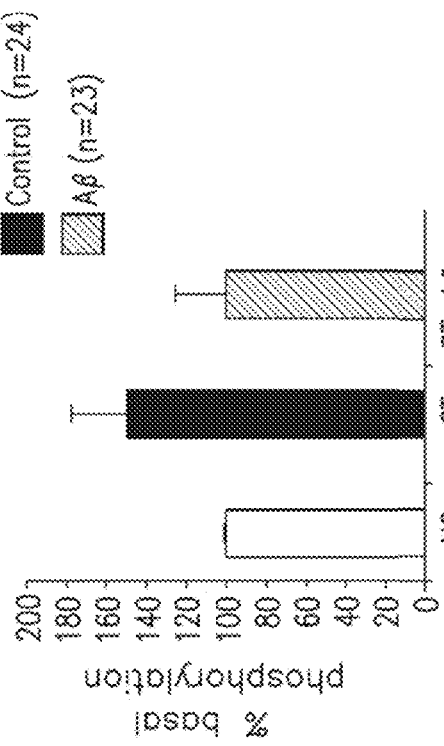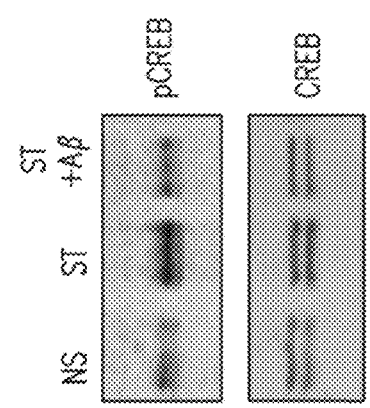

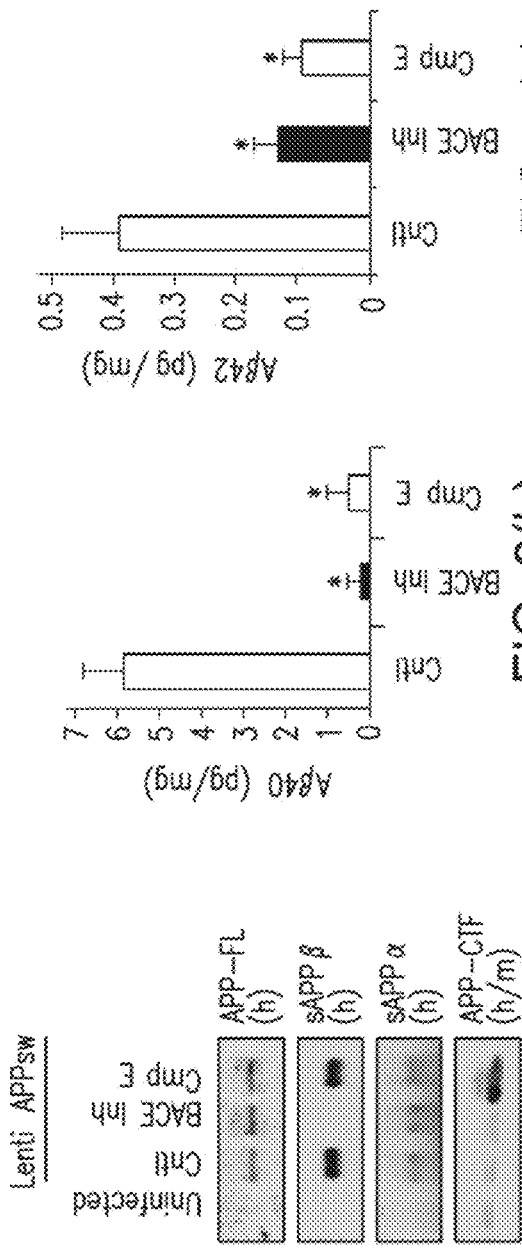
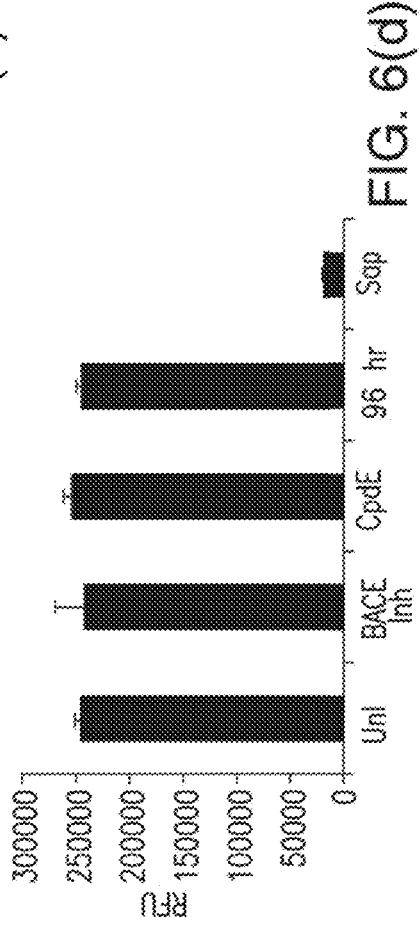
FIG. 6(a)
FIG. 6(b)
FIG. 6(c)
FIG. 6(d)

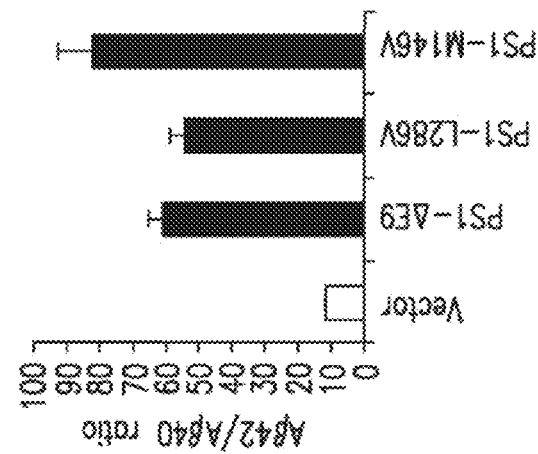
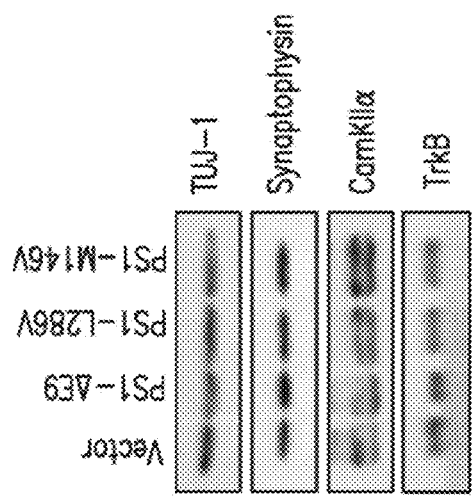
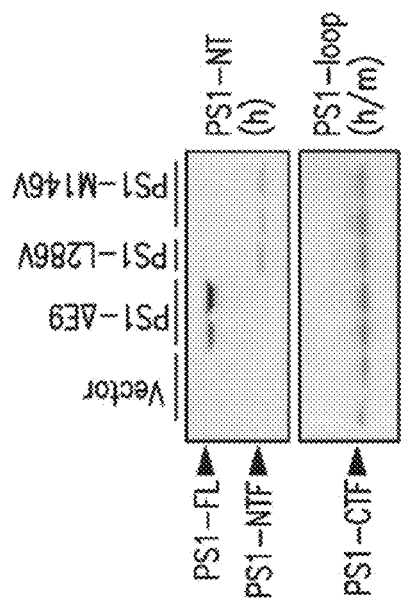
FIG. 7(a)
FIG. 7(b)
FIG. 7(c)

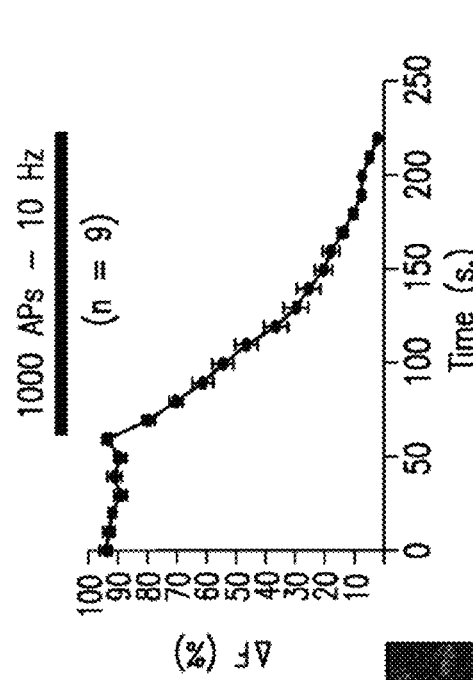
FIG. 8(d)
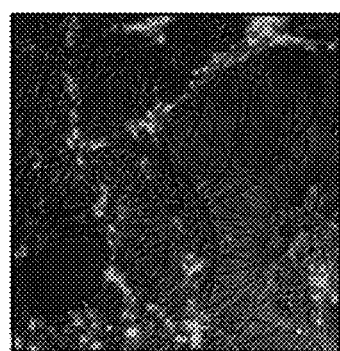
FIG. 8(c)
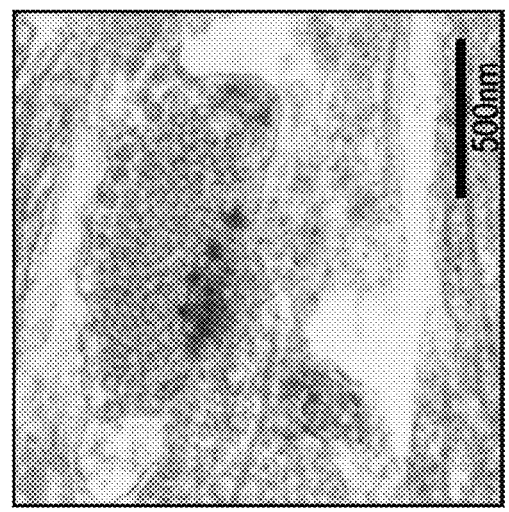
FIG. 8(b)

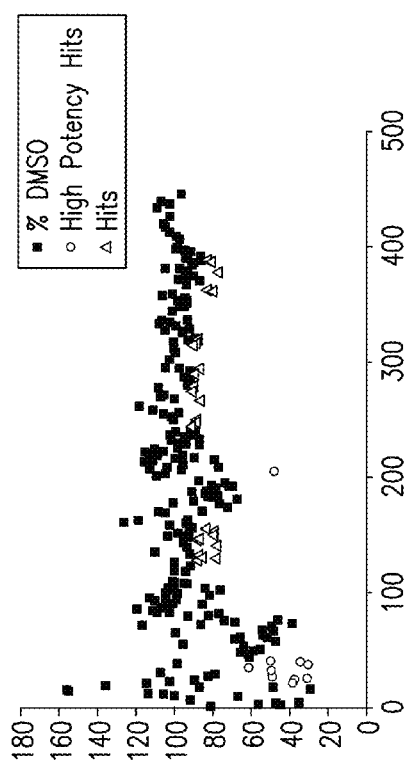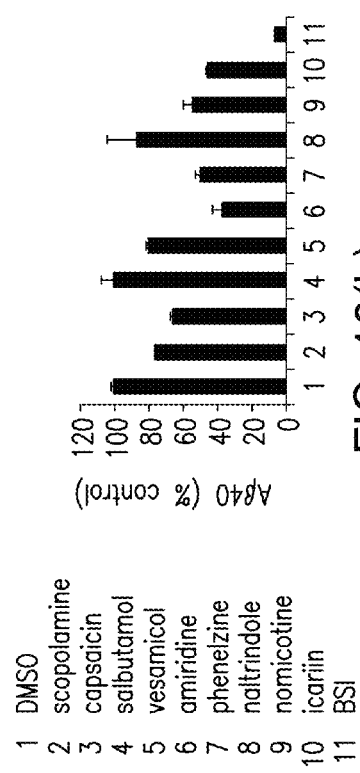

METHODS OF REDUCING LEVELS OF TAU

CROSS-REFERENCE TO RELATED APPLICATIONS

This application is a continuation of PCT App. No. PCT/US12/28345, filed on Mar. 8, 2012, which claims priority to U.S. Provisional App. Ser. No. 61/450,615, filed Mar. 8, 2011, the disclosures of both of which are hereby incorporated by reference in their entirety.

GRANT INFORMATION

The subject matter of this application was developed at least in part using National Institutes of Health Grant Nos. NS051186 and AG033199, so that the United States Government holds certain rights herein.

1. INTRODUCTION

Successful CNS drug discovery requires a scalable, highly physiological neuronal model. Using directed differentiation of mouse embryonic stem (mES) cells, including mES cells isolated from a mouse model of Alzheimer's disease (AD), a highly homogeneous primary neuronal model amenable to phenotypic assays for production and synaptotoxicity of amyloid β-peptide was developed. This model furnishes a highly physiological and AD-relevant platform suitable for high throughput small molecule and functional genetic screens.

2. BACKGROUND OF THE INVENTION

A major obstacle in drug discovery for Alzheimer's disease (AD) and other CNS disorders is the lack of a renewable source of scalable, high quality neuronal cells that recapitulate the pathophysiology of the target disease. Immortalized or genetically transformed neuronal lines generally lack important physiological properties of primary neurons. However, physiologically relevant dissociated primary neuron cultures are limited by cellular heterogeneity, cell number and scalability (Pouton, C. W. & Haynes, J. M. Nat. Rev. Drug. Discov. 6, 605-616 (2007)).

In addition to the issues surrounding physiologically relevant dissociated primary neuron cultures, it is also known that in AD, elevation of amyloid β-peptide (Aβ) and Aβ-triggered synaptic dysfunction are key pathogenic phenotypes (Hardy, J. & Selkoe, D. J. Science 297, 353-6 (2002)). Aβ is produced by sequential proteolytic cleavage of β-amyloid precursor protein (APP) by a set of membrane-bound proteases termed β- and γ-secretases. Various therapeutic approaches for AD are currently under development and include compounds that target β-amyloid pathway (Mangialasche, F., Solomon, A., Winblad, B., Mecocci, P, & Kivipelto, M. Lancet Neurol. 9, 702-16 (2010)). Accordingly, it will be important that any renewable source of scalable, high quality neuronal cells that recapitulate the pathophysiology of the target disease also recapitulate the targeted β-amyloid pathway.

The instant invention addresses both of these issues by providing highly physiological and AD-relevant platforms that are suitable for high throughput small molecule and functional genetic screens, as well as providing specific small molecule compounds identified by such screens.

3. SUMMARY OF THE INVENTION

In certain embodiments, the present invention is directed to neuronal compositions that can effectively recapitulate AD pathophysiology, such as, but not limited Aβ biogenesis and Aβ-associated synaptotoxicity, or tau metabolism, including levels of total tau, disease-associated phosphorylated or presence of modified forms of tau. In certain embodiments such neuronal compositions comprise induced pluripotent cells. In certain embodiments, such neuronal compositions comprise induced pluripotent cells derived from Alzheimer disease models. In certain embodiments, such neuronal compositions comprise induced pluripotent cells derived from mouse Alzheimer disease models. In certain embodiments, such neuronal compositions comprise mES cells derived from mouse Alzheimer disease models.

In certain embodiments, the present invention is directed to neuronal compositions that can effectively recapitulate AD pathophysiology, such as, but not limited Aβ biogenesis and Aβ-associated synaptotoxicity or tau metabolism, including levels of total tau, disease-associated phosphorylated or presence of modified forms of tau, and methods of using the same in the context of large scale drug or functional screening to identify modulators. In certain embodiments such neuronal compositions comprise induced pluripotent cells. In certain embodiments, such neuronal compositions comprise induced pluripotent cells derived from Alzheimer disease models. In certain embodiments, such neuronal compositions comprise induced pluripotent cells derived from mouse Alzheimer disease models. In certain embodiments, such neuronal compositions comprise mES cells derived from mouse Alzheimer disease models.

In certain embodiments, the present invention relates to a method of reducing pathological changes in tau metabolism, including levels of total tau, disease-associated phosphorylated or modified forms of tau comprising administration of an inhibitor selected from the group consisting of: pargyline; deprenyl; propargyl; S2101; pyradin; disulfiram; and ebselen.

In certain embodiments, the present invention relates to a method of reducing pathological changes in APP metabolism comprising administration of an inhibitor selected from the group consisting of the compounds identified in Table 1. In certain embodiments, the inhibitor is selected from the group consisting of: phenelzine, icariin, and amiridine.

In certain embodiments, the present invention relates to a method of treatment or prevention of Alzheimer's disease comprising administration of an inhibitor selected from the group consisting of pargyline; deprenyl; propargyl; S2101; pyradin; disulfiram; and ebselen.

In certain embodiments, the present invention relates to a method of treatment or prevention of Alzheimer's disease comprising administration of an inhibitor selected from the group consisting of the compounds identified in Table 1. In certain embodiments, the inhibitor is selected from the group consisting of: phenelzine, icariin, and amiridine.

In certain embodiments, the present invention relates to a method for identifying inhibitors of APP metabolism comprising: preparing a neuronal model by directed differentiation of ES cells into pyramidal neurons; contacting said neuronal model with a putative inhibitor of APP metabolism; comparing the level and nature of APP metabolism of said neuronal model with the level and nature of APP metabolism of said neuronal model in the absence of said putative inhibitor of APP metabolism; wherein a decrease in the level or nature of APP metabolism in said neuronal model contacted with said putative inhibitor of APP metabolism as compared to said neuronal model in the absence of said putative inhibitor of APP metabolism is indicative that the putative inhibitor is an APP metabolism inhibitor.

In certain embodiments, the present invention relates to a method for identifying inhibitors of tau metabolism comprising: preparing a neuronal model by directed differentiation of ES cells into pyramidal neurons; contacting said neuronal model with a putative inhibitor of tau metabolism; comparing the level and nature of tau metabolism of said neuronal model with the level and nature of tau metabolism of said neuronal model in the absence of said putative inhibitor of tau metabolism; wherein a decrease in the level or nature of tau metabolism in said neuronal model contacted with said putative inhibitor of tau metabolism as compared to said neuronal model in the absence of said putative inhibitor of tau metabolism is indicative that the putative inhibitor is an tau metabolism inhibitor.

4. BRIEF DESCRIPTION OF THE FIGURES

FIGS. 1(a)-(e). Directed differentiation of mES cells into pyramidal cell-enriched neurons (a) Schematic of the differentiation procedure [primary mouse embryonic fibroblasts (pMEF) and retinoic acid (RA)]. (b) ES cell derived neuronal culture at DIV 7 co-labeled with neuronal β-tubulin III (TUJ1), EMX1 antibodies and DAPI to identify nuclei. (c) ES cell derived neuron culture at DIV 7 co-stained with GFAP antibody and TUJ1 antibodies and DAPI to identify nuclei. (d) Quantification of stained cultures show only 6 (+/−1.5) % of DAPI labeled cells stained positive for GFAP, while 68 (+/−10)% cells were positive for EMX1 and 89.5 (+/−4)% cells were positive for TUJ1. Scale bar represents 40 μm. (e) Cultures increasingly express neuronal proteins assessed by Western analysis using indicated antibodies.

FIGS. 2(a)-(j). Characterization and miniaturization of phenotypic assay for Aβ production in ES cell-derived neurons (a) ES cells and ES-cell derived pyramidal neurons at 7, 14 and 21 DIV. APP, BACE1 and PS1-CTF detected by Western blot analysis of the cell lysates using indicated antibodies. (b) Cell lysates from DIV 7 Tg2576 ES-derived neurons treated with indicated compounds were subjected to Western blot detection with 6E10 (APP-FL), APP-CTmax (APP-CTF) and antibodies to indicated proteins. (c) Secreted sAPPα and APPP were immunoprecipitated from conditioned medium after treatment of Tg2576 ES-derived neurons with the indicated compounds. (d-e) Secreted Aβ levels are shown in pg/ml+s.d. Aβ40 and Aβ42 were detected using human specific Aβ40 or 42 ELISA kit. The values were normalized to the protein concentration of the neurons and ** indicates p<0.01. (f) DIV 8Tg2576 ES-derived neurons were plated at increasing density in a 96 well plate and subjected to a cell viability assay quantified in relative fluorescent units (RFU). (g-h) % CV and (h) Z' were calculated with increasing number of wells. The minimum % CV and maximum Z' are optimized at n=5 wells at a plating density of 1.5×105 cells/cm2 (arrows in g and h). (i-j) Tg2576 ES-derived neurons were treated with indicated compounds. Data are the mean of results from 5 wells except DMSO (n=8) and SEM is shown by error bars.

FIGS. 3(a)-(l). Modeling Aβ-associated synaptic abnormalities in ES cell-derived neurons. (a-b) At DIV 21 mES derived neurons were treated for 24 hours with control or Aβ42 oligomer, subsequently fixed and co-stained for synaptic proteins PSD-95 (green) and synaptophysin (S-physin) (red). Nuclei are labeled with DAPI (blue). PSD-95 and S-physin particles were analyzed using Image J software. (c-f) Quantification of PSD-95 positive particles and synpatophysin positive particles using Image J software particle analysis. (g) DIV 21 ES cell-derived neurons were treated with control or Aβ42 oligomer, fixed, DiI labeled and imaged with confocal microscopy. (h-j) Spine density, length and dendrite diameter were quantified. (k) Phosphorylation of CREB was detected with a pCREB specific antibody after stimulation of cultures with or without Aβ42 oligomer pretreatment. (l) Quantification of CREB and pCREB using infrared quantitative Western blot imaging system with SEM shown by error bars.

Figures 4A, 4B, 4C:
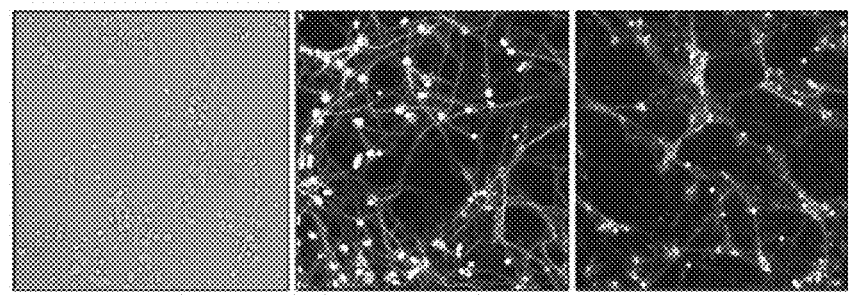

FIGS. 4(a)-(c). mES derived neurons display neural morphology and express neural proteins. (a) Majority of cells in phase contrast image of mES derived neurons at day 5 of differentiation show neuronal morphology. (b) Same neuronal culture at DIV 8, nuclei are labeled with DAPI (red) and neurons are stained with an antibody recognizing neuronal protein MAP2B (green). (c) Same culture at DIV 8, nuclei are labeled with DAPI (blue) and neuronal β-tubulin (TUJ-1) (green).

Figure 5A:
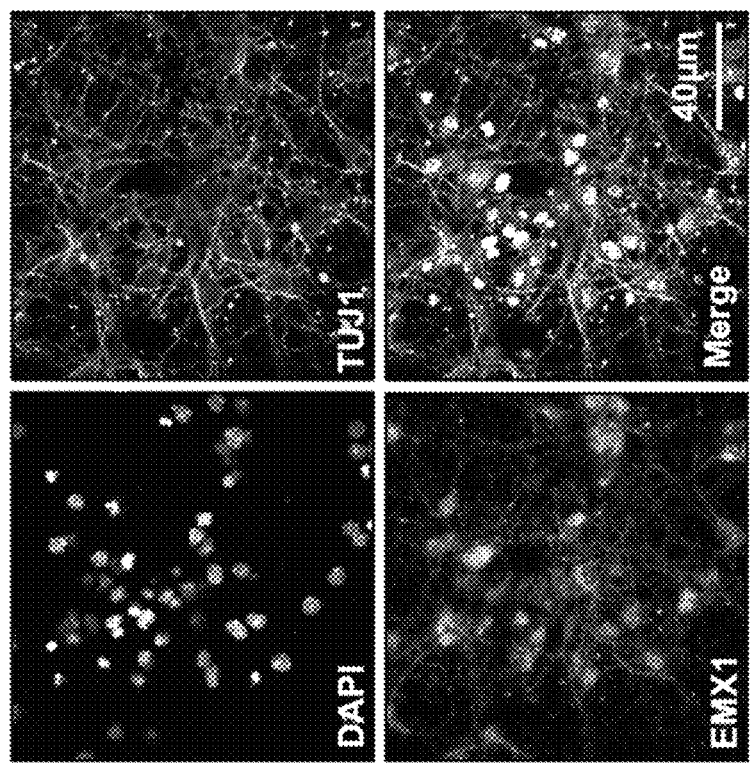
Figure 5B:
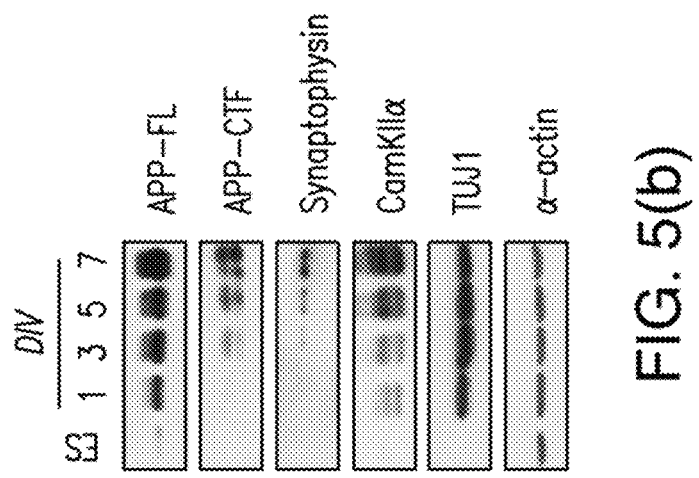

FIGS. 5(a)-(b). Neurons derived from mES cells isolated from Tg2576 blastocysts display neuronal morphology and express neuronal proteins. (a) Tg2576 mES derived neurons express neuronal β-tubulin (TUJ-1) (green) and pyramidal cell protein EMX1 (red). Scale bar represents 40β. (b) Western blot analysis of protein lysates from Tg2576 mES-derived neuronal culture harvested at indicated DIV express APP, cleaved APP fragments (APP-CTF) and neuronal proteins synaptophysin, CamKIIα, and neuronal β-tubulin (TUJ-1). α-Actin is a loading control.

FIGS. 6(a)-(d). Neurons derived from mES cells infected with APPsw lenti virus effectively process APP. (a) Western blot analysis of protein lystates from mES cell derived neurons infected with lenti virus harboring human APPsw express APP and proteolytic fragments. Secreted APP fragments, SAPPβ and SAPPα, were immunoprecipitated from condition media and APP and CTFs were detected in cell lysates. (b-c) Aβ40 and Aβ42 were detected in conditioned medium using human specific ELISA and values were normalized to a protein lysate concentration. (d) APPsw lenti viral infected mES cell derived neurons were subjected to a fluorescent cell viability assay (Cell Quanti Blue) and relative fluorescent units (RFU) are shown. Neurons were either uninfected (Uni) or infected with APPsw lenti virus for 24 hours and 48 hours after initial infection, treated with BACE inhibitor (BACE inh), γ-secretase inhibitor (CpdE) for 24 hours. Neurons infected for 96 hours (96 hr) did not show loss in cell viability.

FIGS. 7(a)-(c). Biochemical confirmation of transgene expression and APP processing in FAD mutant cells. (a) three different FDA mutants of PS1 (AE9, M146V, and L286V) were introduced into mES cells by electroporation followed by antibiotic-resistance selection. The resulting mES cells were subjected to directed differentiation into pyramidal neurons. A representative Western blot shows transgene expression in the neurons derived from these clonal mES cell lines using an anti-human PS1 specific antibody. (PS1-NT, provided by J. Lah, Emory University). (b) PS FAD-expressing cells undergo normal directed differentiation into pyramidal neurons. (c) ELISA detection of Aβ40 and Aβ42 from conditioned media of mES cell derived neurons stably expression PS-FAD mutants infected at DIV 7 or 14 neurons with APPsw lentiviral particles resulted in enhanced ratio of Aβ40/Aβ42.

FIGS. 8(a)-(d). Synapses from mature mES derived neurons express pre- and post-synaptic proteins; and are morphologically and functionally intact. (a) Confocal images of DIV 21 neurons derived from mES cells detect post-synaptic density protein PSD-95 and pre-synaptic density protein synaptophysin which localize to adjacent puncta at higher magnification. (b) Electron micrograph showing intact synaptic structures including post-synaptic density and pre-synaptic vesicles in DIV 21 cultures. (c) Activity-dependent FM 4-64 update and unloading due to electrical stimulation. (d) Internalized dye was released by 1000 stimulations at 10 Hz.

Figure 9:
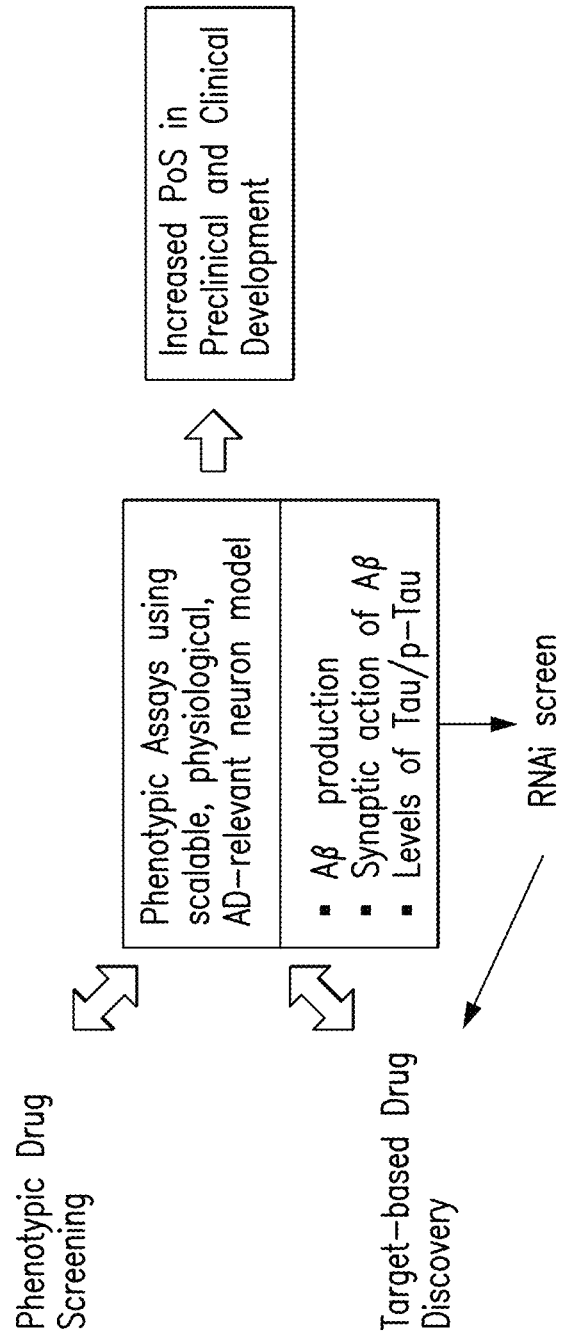

FIG. 9. Modeling AD using Stem cell-derived neurons.

FIGS. 10(a)-(b). Results from screen of ES neurons for compounds which reduce Aβ40. The screening assay described Example 2, below, was used to conduct screening of compound library for small molecule inhibitors of Aβ production. (A) Aβ40 production (% control) of compounds in the screen by number. Hits were determined to be compounds which reduced Aβ40 by three standard deviations (SD) but did not cause a change in metabolism or viability by more than 2 SD from the mean. (B) Confirmed hits were used to treat neurons in 12-well plates at 10 μM and Aβ40 production was determined using ELISA.

Figure 11:
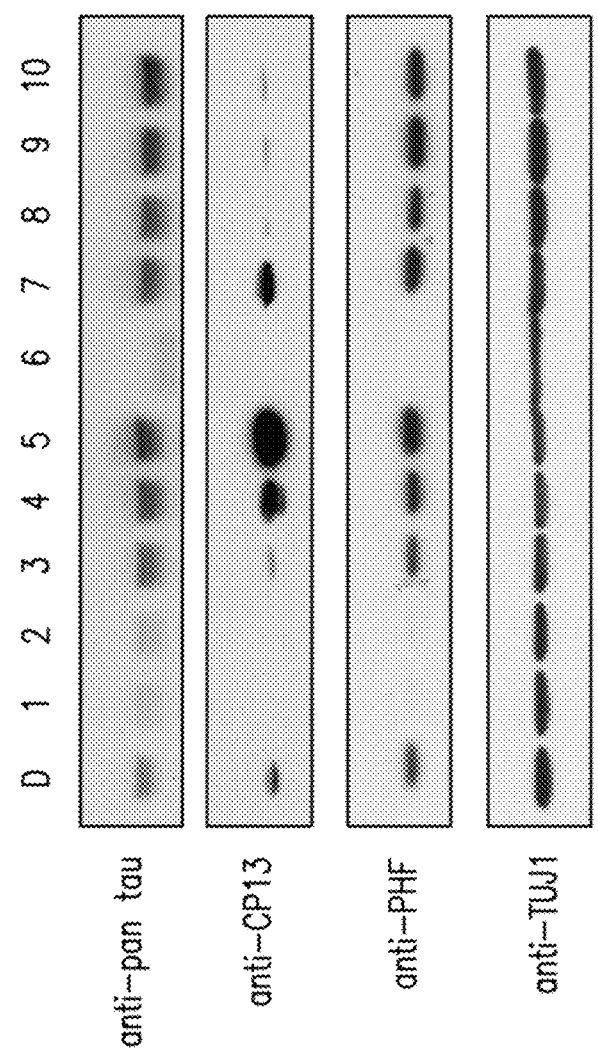

FIG. 11. Wild type, mouse embryoinc stem cells were differentiated into pyramidal neurons using the protocol described in the Examples section. ES cell-derived neurons were treated at 14 DIV for 48 hr with either vehicle (D, DMSO) or various histone demethylase inhibitors (1-10). Tau isoforms were detected by Western blot analysis of the cell lysates using the indicated antibodies. CP13 recognizes tau phosphorylation at ser202/205. PHF recognizes tau phosphorylation at ser396/404. TUJ1 (Neuron-specific class III beta-tubulin) is used as a loading control. List of compounds tested for their ability to inhibit levels of total tau, disease-associated phosphorylated or presence of modified forms of tau include (asterisk denotes hit compounds): *1. pargyline (LSD1 inhibitor)—1000 uM; *2. deprenyl (LSD1 inhibitor)—1000 uM; *3. propargyl (LSD1 inhibitor)—100 uM; 4. phenelzine (LSD1 inhibitor)—100 uM; 5. tranylcyprmine (LSD1 inhibitor)—200 uM; *6. S2101 (LSD1 Inhibitor II, EMD Biosciences catalog #489477)—LSD1 inhibitor—1 uM; 7. N-oxyalylglycine (NOG) (JMJD2s inhibitor)—1000 uM; *8. pyradine (JMJ2A and E inhibitor)—1000 uM; *9. disulfiram (JMJ2A inhibitor)—20 uM; *10. ebselen (JMJ2A inhibitor)—20 uM.

5. DETAILED DESCRIPTION OF THE INVENTION

5.1. Neuronal Models and their Use

Successful CNS drug discovery requires a scalable, highly physiological neuronal model. In certain embodiments of the present invention, such models are developed using directed differentiation of mouse embryonic stem (mES) cells. For example, in certain non-limiting examples, such embodiment can include mES cells isolated from a mouse model of Alzheimer's disease (AD), which furnishes a highly physiological and AD-relevant platform suitable for high throughput small molecule and functional genetic screens. In alternative embodiments, the platform will make use of induced pluripotent stem cells derived from Alzheimer research models other than mES cells.

To establish an non-limiting example of an AD-relevant neuronal model, a phenotypic cell-based assay for either the biogenesis or synaptic action of Aβ using mouse ES cell-derived primary neuronal cultures highly enriched in functional pyramidal neurons was developed. Pyramidal cells represent one of the most vulnerable populations of neurons in AD (Mann, D. M. Neurodegeneration. 5, 423-7 (1996)). To produce a neuronal culture highly enriched in pyramidal cells, directed differentiation of mES cells was induced by modifying published protocols (FIG. 1a). Obvious neuronal morphology could be identified within 24 hours after dissociation and plating embryoid bodies, day in vitro (DIV) 1, and most cells displayed neuronal morphology by DIV 5 (FIG. 4a). Labeling DIV 7-8 neurons with antibodies recognizing pan neuronal markers, microtubule associated protein 2B (FIG. 4b) and neuronal β-tubulin (TUJ-1), (FIG. 4c and FIG. 1b-d) as well as pyramidal neuron marker EMX1 (FIG. 1b,d) substantiated a highly homogenous neuronal population enriched in pyramidal neurons. Glial cells, identified by the presence of Glial Fibrilary Acidic Protein (GFAP) are only rarely observed (FIG. 1 c, d). The neuron specific proteins neuronal β-tubulin (TUJ-1) and synaptophysin as well as glutamatergic neuronal proteins such as TrkB and CamKIIα increase from DIV 1-7 (FIG. 1e). Consistent with maturing pyramidal neurons, there is a gradual decline in the levels of the p75 neurotrophin receptor (p75NTR) (Bibel, M., et al. Nat. Neurosci. 7, 1003-9 (2004)).

Although the instant application includes working examples relating specifically to detection of proteolytic derivatives of APP, including Aβ, as well as to tau metabolism, including levels of total tau, disease-associated phosphorylated or presence of modified forms of tau, the models described herein are not limited to those particular assays. In particular, the models of the instant application can be employed for a wide variety of high throughput compound screens as well as genetic screening.

The reliable detection of proteolytic derivatives of APP, including AP, is critical for a physiologically relevant cell based AD model. It was established that ES cell-derived pyramidal neurons express the major proteolytic enzymes mediating APP processing, β-site APP cleaving enzyme (BACE1) and presenilin 1 (PS1) (FIG. 2a). Endogenous APP, BACE1 and PS1 were abundantly detected in ES cell-derived pyramidal neurons at DIV 7, 14, 21. APP and BACE1 were not detected in ES cells, but PS1 was detectable consistent with it's described role in development (Wong, P. C. et al. Nature 387, 288-292 (1997)). To achieve robust and reproducible neuronal expression of human APP, ES cells from the inner cell mass of blastocysts were isolated from a well characterized mouse model of AD, Tg2576. Tg2576 mice express human APP, harboring the Swedish mutation (APPsw) under the control of hamster PrP promoter (Hsiao, K. et al. Science 274, 99-102 (1996)). Characterization of mES cell-derived neurons showed normal neuronal differentiation by morphology and neuronal protein expression (FIG. 5a) indicating that the APP transgene does not interfere with neuronal differentiation of ES cells. Neuronal proteins synaptophysin, neuronal β-tubulin (TUJ-1), and CamKIIα showed increased expression from DIV 1-7 (FIG. 5b) similar to wild-type mES cell neurons. The transgene human APPsw was detected with the human-specific APP antibody 6E10, revealing increased expression of APP from DIV 1-7, but little expression in the undifferentiated ES cells (FIG. 5b). In Tg2576 ES cell derived neurons, APP cleavage products were readily detectable. C-terminal APP fragments (CTFs) were detected in the neuronal lysate by Western blot analysis (FIG. 2b). Both human β- and α-secretase-derived secreted soluble APP (sAPPβ and sAPPα, respectively) were detected using immunoprecipitation of conditioned medium with sβsw and Aβ levels were detected in conditioned media using a human Aβ specific ELISA (FIG. 2b-e). Treatment of these neurons with a commercial BACE1 inhibitor decreased the secretion of sAPPβ, Aβ40 and Aβ42 while treatment with a γ-secretase inhibitor, Compound E, inhibited Aβ40 and Aβ42 secretion without affecting the levels of sAPPβ or sAPPα (FIG. 2b-e). Treatment of neurons with an α-secretase inhibitor, TAPI-2, resulted in a decrease of sAPPα (FIG. 2c) level. Consistent with previous studies in cell models and mouse brain, CTFs resulting from APP cleavage, accumulated in response to γ-secretase inhibitor treatment (FIG. 2b). Identical results were seen when neurons were infected with an APPsw Lenti virus and APP processing was analyzed (FIG. 6a-c). Lentiviral gene transfer did not affect the viability of mES cell-derived neurons (FIG. 6d). Thus, these neurons are suitable for lentiviral mediated genetic manipulation studies.

A major advantage of a stem cell based neuronal model is that genetic manipulation at the ES cell stage, permits stable expression in karyotypically normal neurons. Three different familial AD (FAD) mutant PS1 (AE9, M146V, and L286V) transgenes were introduced into mES cells by electroporation and transduced cells were subjected to antibiotic-resistant selection. Resulting mES cells were subjected to directed differentiation into pyramidal neurons. A representative Western blot shows the PS1 transgene and normal neuronal protein expression in neurons derived from these clonal mES cell lines (FIG. 7a,b). An increase in the Aβ42/Aβ40 ratio, a key pathogenic phenotype associated with PS1 FAD (Hardy, J. & Selkoe, D. J. Science 297, 353-6 (2002)), was observed in mES cell-derived neurons expressing ΔE9 M146V, and L286V mutant forms of PS1 (FIG. 7c). This data validates the concept that differentiated neurons harboring mutant transgenes can recapitulate the disease phenotype.

Figure 2J:
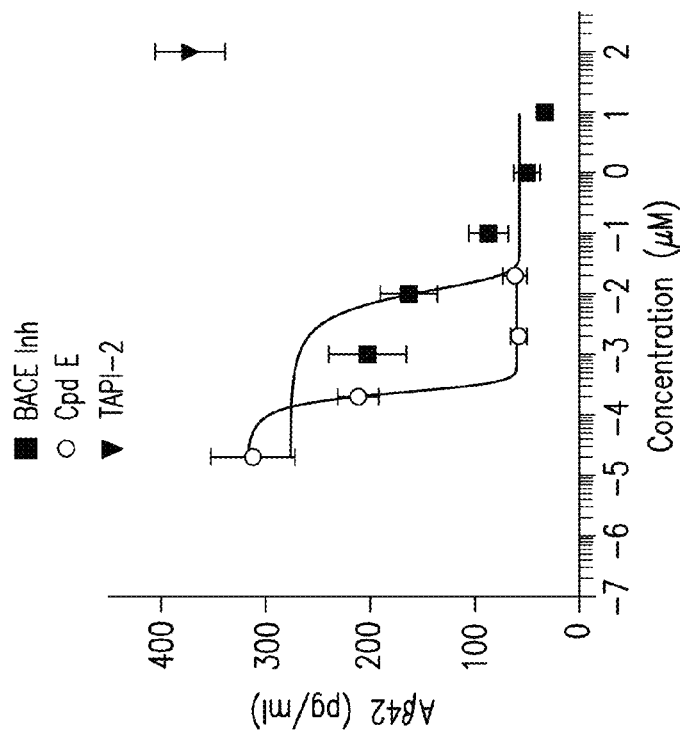
Figure 2I:
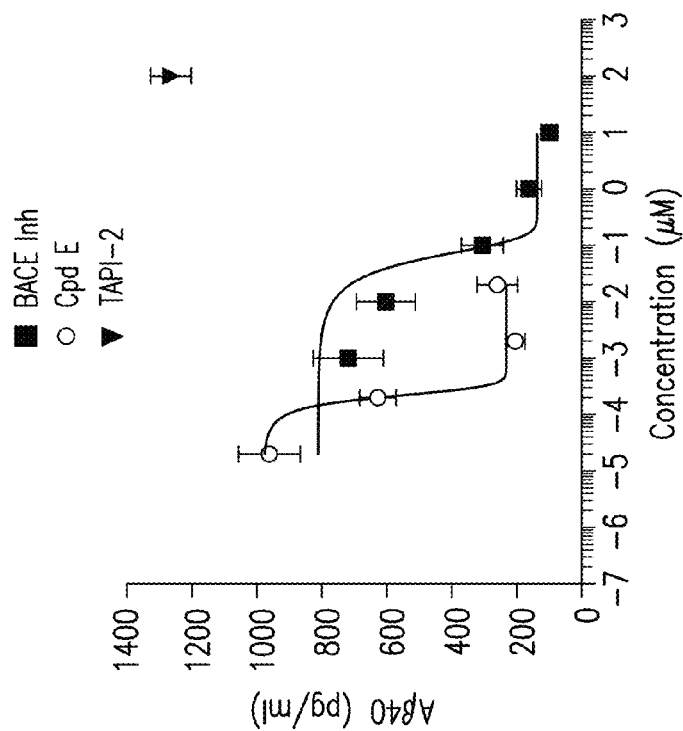

To accommodate high-throughput screening, Aβ detection assays using the Tg2576 mES cell derived neurons were miniaturized for a 96 well platform. Cell density was first optimized using a resorufin based cell viability assay (FIG. 2f). It was determined that the optimal cell density of $1.5 \times 10^5$ cells/cm$^2$ maximized the cell viability signal. The assay was next optimized based on two parameters: minimizing the coefficient of variance (% CV) and maximizing Z' factor (Inglese, J. et al. Nat Chem Biol. 3, 466-79 (2007)). Increasing the number of replicate wells enhances both % CV and Z' factor values and at the plating density of $1.5 \times 10^5$ cells/cm$^2$, with 5 replicate wells, both the % CV (FIG. 2g, h) and Z' factor are optimized (FIG. 2h). Using the optimized 96 well platform, mES displayed characteristic inhibitor response kinetic profiles for both BACE1 inhibitors and γ-secretase inhibitor, Compound E (FIGS. 2i and 2j; Stachel, S. J. et al. Bioorg. Med. Chem. Lett. 16, 641-4 (2006), and Seiffert, D. et al. J. Biol. Chem. 275, 34086-91 (2000)) IC50 values for a BACE inhibitor were 44.7 nM and 7.8 nM for Aβ40 and Aβ42 respectively. IC50 values for Compound E were 200 pM for both Aβ40 and Aβ42 (Stachel, S. J. et al. Bioorg. Med. Chem. Lett. 16, 641-4 (2006), and Seiffert, D. et al. J. Biol. Chem. 275, 34086-91 (2000)). Thus, the miniaturized neuronal Aβ assay using Tg2576 mES-derived neurons is robust, reliable and suitable for HTS campaign.

Figure 8A:
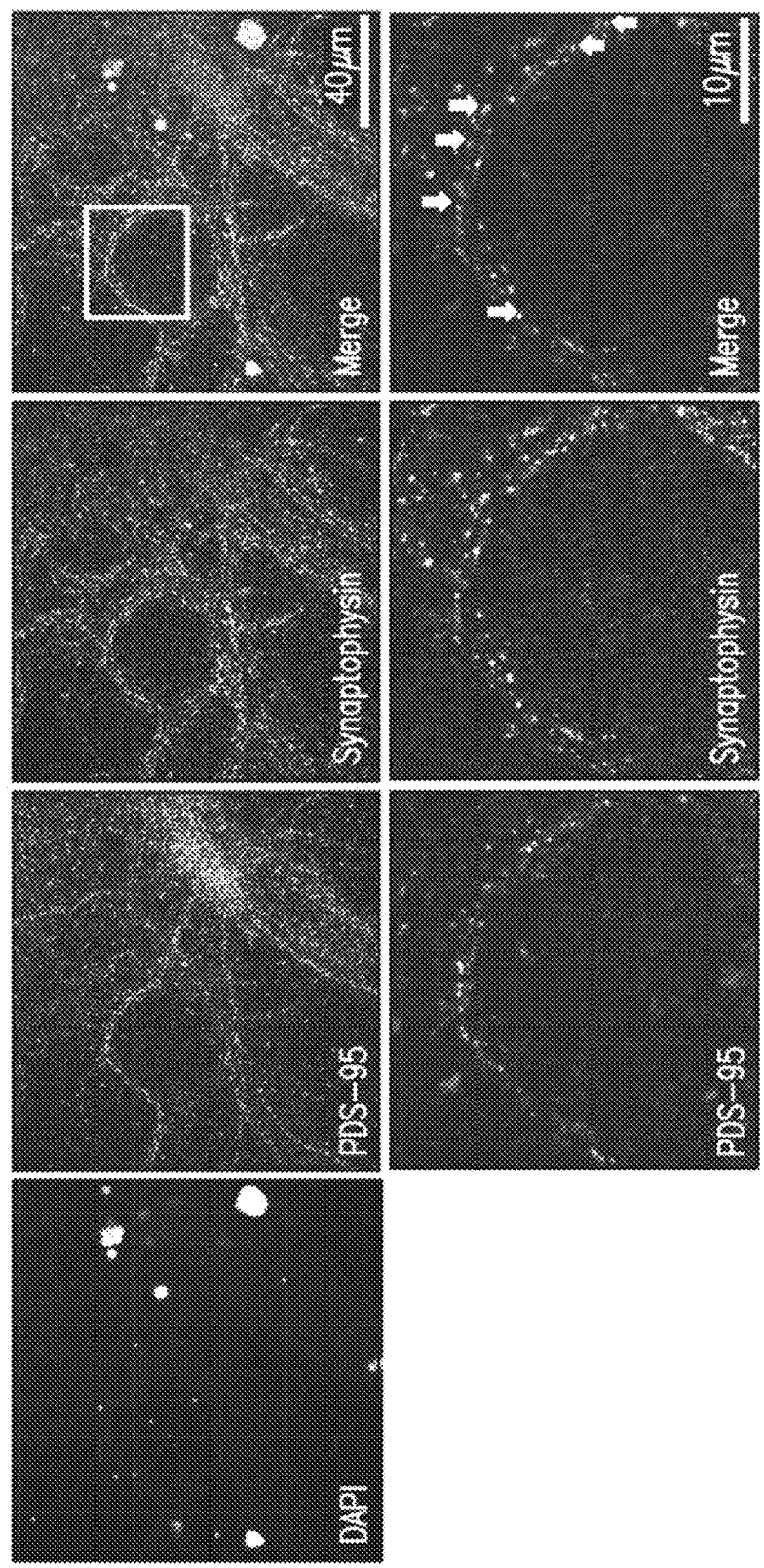

Formation of morphologically and functionally intact synapses is a key feature of a robust primary neuronal model. To determine whether ES cell-derived neurons form synapses that are morphologically and functionally intact, immunocytochemical analysis of pre- and postsynaptic markers, synaptophysin and PSD95, respectively was performed. The subcellular distribution of endogenous synaptophysin and PSD95 recapitulated mature synapses in primary neurons (FIG. 8a). High magnification confocal microscopy showed small adjacent punta of synaptophysin and PSD95, indicative of synaptic terminals, along dendritic processes of mES-derived pyramidal neurons (FIG. 8a).

Subsequent electron microscopy (EM) analysis revealed that both presynaptic vesicles as well as dense postsynaptic densities were apparent in this culture (FIG. 8b). The synapses are also functional and display, activity-dependent FM 4-64 uptake and unloading due to electrical stimulation DIV 18-21 (FIG. 8c). The data indicates that mES cells form robust synaptic connections in contrast to human ES cell-derived neurons which requireadditional genetic manipulation (Kim, J. E. et al. Proc Natl Acad Sci USA 108 3005-10 (2011)).

Figure 3A:
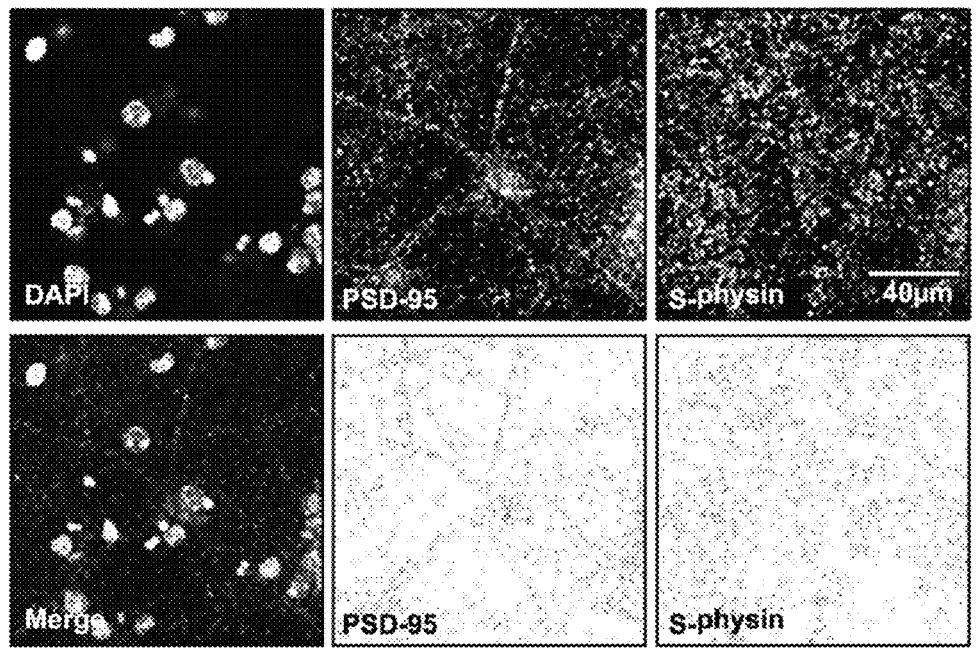
Figure 3B:
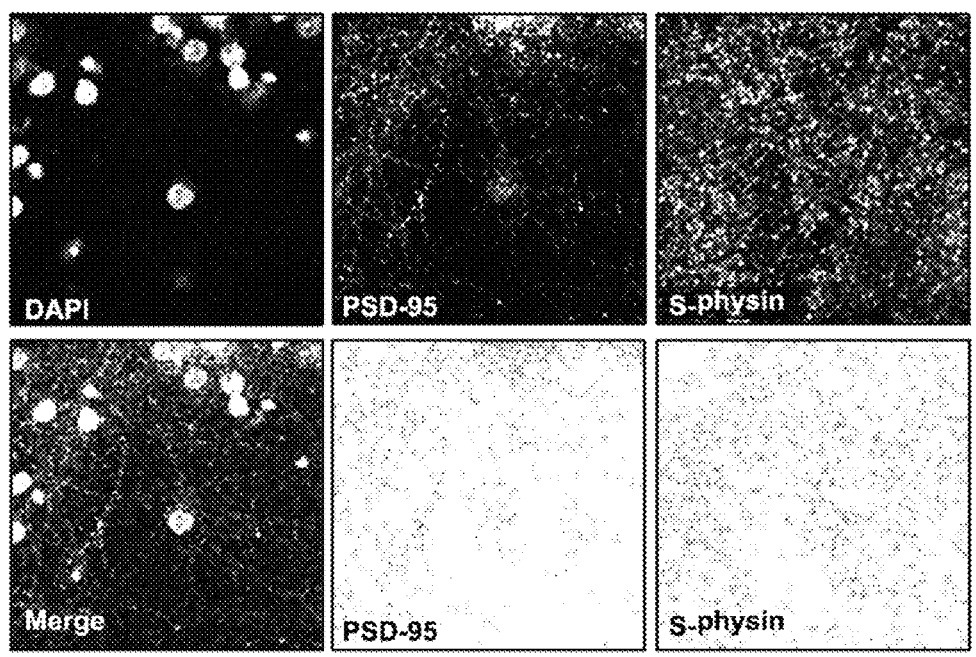
Figure 3C:
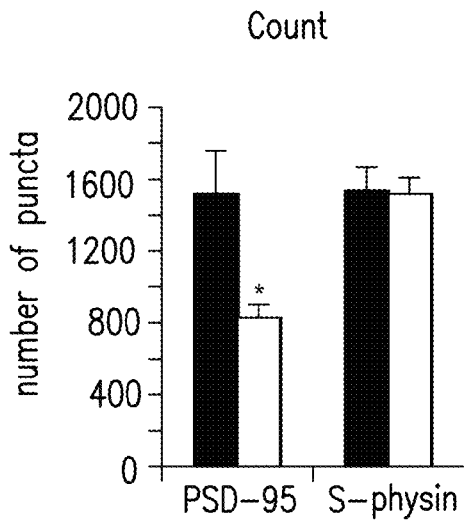
Figure 3D:
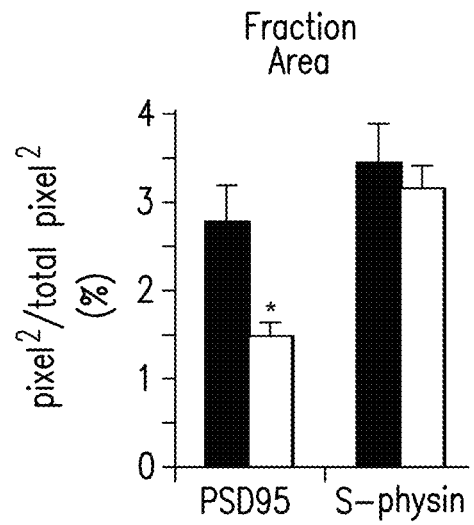
Figure 3E:
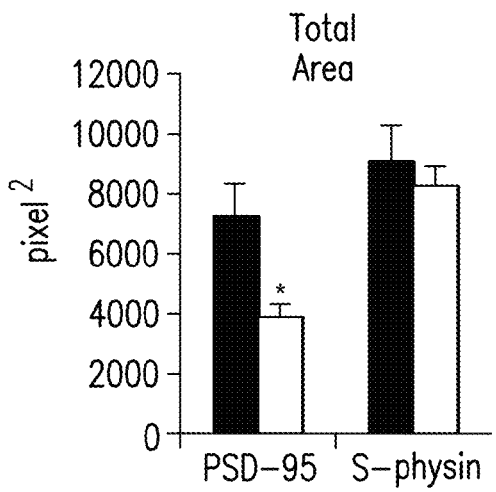
Figure 3F:
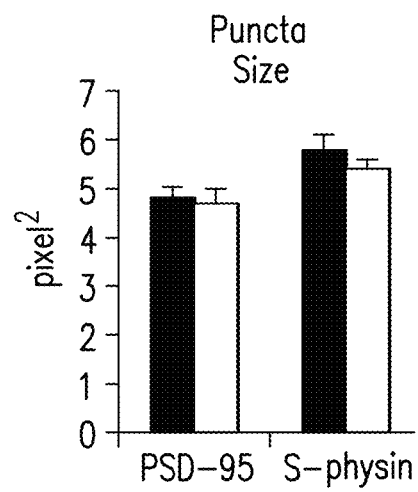
Figure 3G:
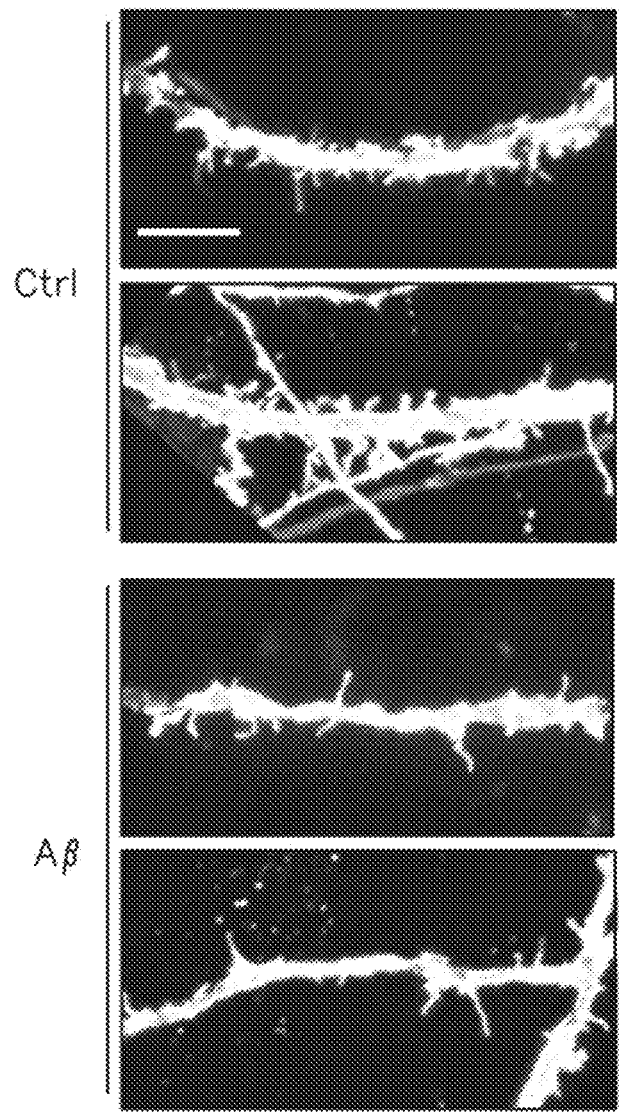

To model Aβ-induced synaptic abnormalities using mES-derived neurons, the effects of Aβ treatment on synaptic morphology and function were examined. Oligomerie Aβ treatment of neurons has been shown to decrease synapse number which correlates with the loss of postsynaptic protein, PSD-95, immunoreactivity (Cerpa, W. et al. Mol Neurodegener. 5, 3 (2010)). To this end, the density of PSD-95 and synaptophysin positive puncta in A13 oligomer-treated neurons was analyzed (FIG. 3a-f). Consistent with published data (Cerpa, W. et al. Mol Neurodegener. 5, 3 (2010)) it was found that oligomeric Aβ treatment leads to the decreased PSD-95 puncta count, total area and fractional area, but the number of synaptophysin puncta remained unchanged (FIG. 3a-f). Thus, selective reduction of PSD95 immunoreactivity in response to Aβ is recapitulated in the ES cell-derived neurons. Additional characteristic synaptic changes associated with Aβ treatment include the reduction in dendritic spine density (Hsieh, H. et al. Neuron 52, 831-43 (2006) and Shankar, G. M. et al J. Neurosci. 27, 2866-75 (2007)). Treatment of mES cell-derived neurons with Aβ oligomers reduced spines identified using DiOlistic labeling (FIG. 3g,h). After Aβ oligomer treatment, spine length increases modestly without affecting dendritic diameter (FIG. 3h-i). In addition to morphological spine changes, at a functional level in neurons, Aβ has been shown to induce characteristic molecular changes, highlighted by the suppression of the phosphorylation of cyclic AMP response element binding protein, CREB, a memory-associated transcription factor (Vitolo O V, et al. Proc Nal Acad Sci USA 99, 13217-21 (2002)). In mES cell-derived neurons, A13 oligomer treatment prevents increased phosphorylation of CREB (pCREB) resulting from NMDA-dependent stimulation (FIG. 3k,l). Thus, the ES cell derived culture described herein offers a highly physiological, homogenous, and scalable neuronal model that can recapitulate key synaptic phenotypes associated with Aβ insult both at the functional and morphological level.

Collectively, the findings described herein indicate that the neuronal models of the instant invention are suitable for functional and pharmacological studies that require abundant and homogenous physiological neurons. In addition, the systems described herein also allow for large scale drug or functional screening to identify modulators that can effectively inhibit Aβ biogenesis and Aβ-associated synaptotoxicity, as well as including levels of total tau, disease-associated phosphorylated or presence of modified forms of tau.

5.2. Inhibitors Identified by the Assays of the Invention

In certain embodiments the instant invention is directed to inhibitors of protein metabolism, for example, but not by way of limitation, Aβ40 production and/or tau metabolism, including levels of total tau, disease-associated phosphorylated or presence of modified forms of tau.

In certain embodiments, the inhibitor of the present invention is identified by an assay directed to detecting inhibitors of Aβ40 production. For example, but not by way of limitation, such assays can include assays such as those prepared as follows. First, mouse ES cells isolated from Tg2576 mice are subjected to directed differentiation as previously described. After dissociation of embryoid bodies, neurons are plated in poly-D-lysine and laminin coated 96 well black plates at a density of 1.5×105 cells/cm2 which is 45,000 cells/well. Media is changed to N2 containing media after 4 hours and again the next day after plating. Two days after plating, media is changed to B27 containing media which is replaced every 2 days after that. On day 8 after plating the mouse ES derived neurons are treated with the compound of interest. For example, in certain embodiments, the inhibitors are from a library of 446 clinically relevant compounds which have a history of use in human clinical trials, the NIH clinical collection (NCC) (http://www.nih-clinicalcollection.com/). In certain embodiments the compounds are incubated with the cells for 24 hours in 150 μl B27 media. In certain embodiments each plate of ES derived neurons is treated with NCC compounds, DMSO (negative control), and the positive controls for Aβ reduction BACE inhibitor IV (Calbiochem) and Compound E. After 24 hours, 100 μl conditioned media can then be removed and frozen at −80° C. until further analysis for Aβ40 content. The remaining cells in 50 μl media can be subjected to cell viability assay CellQuanti Blue (BioAssay Systems). In certain embodiments, conditioned media can be subjected to Aβ40 quantification, e.g., by using Aβ40 ELISA (Invitrogen). Compounds which lower Aβ40 levels in the conditioned media can then be identified.

In certain embodiments, the inhibitors of the instant invention are inhibitors of Aβ40 production. In certain embodiments, a hit is defined as an inhibitor capable of lowering Aβ by 4 standard deviations below the negative control (e.g., DMSO or other inactive carrier substance) treated condition. In certain embodiments, the hit can achieve this amount of Aβ40 lowering, yet maintains cell viability within 2 standard deviations of control. In certain embodiments, a hit is defined by the ability to lower Aβ40 40% or more. In certain embodiments the inhibitor is: phenelzine (IC50 2.5 μM); icariin (IC50 5.1 μM) or amiridine (IC50 2.3 μM).

In certain embodiments the inhibitor is selected from the list of compounds presented in Table 1.

TABLE 1

| Percent Inhibition | |
|---|---|
| | High potency hits |
| 40% | amiridine (cyclopenta[b]quinolin-9-amine, 2,3,5,6,7,8-hexahydro-,monohydrochloride) |
| 53% | icariin |
| 70% | phenelzine sulfate |
| 70% | salbutamol sulfate |
| 52% | vesamicol hcl |
| 50% | pyridazinone, 6-[4-difluoromethoxy)-3-methoxyphenyl] |
| 66% | naltrindole |
| 50% | nornicotine |
| 67% | benzeneacetic acid, alpha-(hydroxymethyl)-, 9-methyl-3-oxa-9-azatricyclo[3,3,1,2,4]non-7-yl ester |
| 62% | capsaicin |

TABLE 1-continued

| Percent Inhibition | |
|---|---|
| | Hits 4 standard deviations lower than DMSO control (per plate) |
| 13% | buflomedil |
| 21% | 4-chloro-n-(2-morpholin-4-yl-ethyl)-benzamide |
| 14% | halometasone |
| 12% | rofecoxib |
| 22% | clarithromycin |
| 11% | piceid |
| 12% | 1-(2-methyl-5-nitro-imidazol-1-yl)-propan-2-ol |
| 20% | megestrol acetate |
| 20% | gabexate mesylate |
| 16% | kitasamycin |
| 8% | sumatriptan succinate |
| 11% | diazepam |
| 11% | peniciclovir |
| 12% | roxatidine acetate |
| 9% | loxoprofen |
| 9.5% | piroxicam |
| 10% | rizatriptan benzoate |
| 13% | nimetanzepam |
| 9% | orinidazole |
| 9% | 1,1,-dimethyl-4-phenylpiperazinium iodide |
| 11% | pirenperone |
| 11.5% | dichloroacetic acid |
| 20% | medroxyprogesterone |
| 17% | pinacicil |
| 17% | 7-nitroindazole |
| 22% | 2h-indol-2-one,1,3-dihydro-1-phenyl-3,3-bis (4-pyridinylmethyl) |
| 19% | cefixime |
| 17% | lofexidine |

In certain embodiments, the inhibitor of the present invention is identified by an assay directed to detecting inhibitors of tau phosporylation. For example, but not by way of limitation, such assays can include assays such as those prepared as follows. First, wild type, mouse embryoinc stem cells are differentiated into pyramidal neurons using the protocol described in Example 1. ES cell-derived neurons are treated at 14 DIV for 48 hr with either vehicle (D, DMSO) or various histone demethylase inhibitors (inhibitor compounds 1-10). Tau isoforms are detected by Western blot analysis of the cell lysates using the indicated antibodies, See FIG. 11. CP13 recognizes tau phosphorylation at ser202/205. PHF recognizes tau phosphorylation at ser396/404. TUJ1 (Neuron-specific class III beta-tubulin) is used as a loading control.

In certain embodiments the inhibitory compound of the present invention is selected from: *1. pargyline (LSD1 inhibitor)—1000 uM; *2. deprenyl (LSD1 inhibitor)—1000 uM; *3. propargyl (LSD1 inhibitor)—100 uM; *6. S2101 (LSD1 Inhibitor II, EMD Biosciences catalog #489477)—LSD1 inhibitor—1 uM; *8. pyradine (JMJ2A and E inhibitor)—1000 uM; *9. disulfiram (JMJ2A inhibitor)—20 uM; and *10. ebselen (JMJ2A inhibitor)—20 uM.

5.3. Treatment of Neurodegenerative Diseases Using the Inhibitors of the Instant Invention In certain embodiments, the present invention provides for methods of treating a neurodegenerative disease in a subject in need of such treatment comprising administering, to the subject, a therapeutically effective amount of at least one compound of Table 1 or FIG. 11. Non-limiting examples of neurodegenerative diseases include Alzheimer's disease, lewy body dementia, inclusion body myositis, and cerebral amyloid angiopathy.

In particular embodiments, the present invention provides for methods of treating diseases related to metabolism of APP by BACE1 or associated with high levels of total tau, disease-associated phosphorylated or presence of modified forms of tau in a subject in need of such treatment by administration of a therapeutic formulation which comprises an effective amount of at least one compound of Table 1 or FIG. 11. In particular embodiments, the formulation may be administered to a subject in need of such treatment in an amount effective to inhibit BACE1 activity and/or reduce the production of sAPPβ and/or Aβ and/or inhibit levels of total tau, disease-associated phosphorylated or presence of modified forms of tau. Where the formulation is to be administered to a subject in vivo, the formulation may be administered systemically (e.g. by intravenous injection, oral administration, inhalation, etc.), intraventricularly, intrathecally, or by any other means known in the art. The amount of the formulation to be administered may be determined using methods known in the art, for example, by performing dose response studies in one or more model system, followed by approved clinical testing in humans.

In certain embodiments, the subject or patient has been diagnosed with, or has been identified as having an increased risk of developing a neurodegenerative disease, such as Alzheimer's Disease.

In certain non-limiting embodiments, the present invention provides for methods of reducing, in a subject, the risk of neural damage related to increased levels of Aβ and/or sAPPβ and/or inhibit levels of total tau, disease-associated phosphorylated or presence of modified forms of tau comprising administering, to the subject, an effective amount of a composition according to the invention. An effective amount may be a local concentration or, in a pharmaceutical composition, an amount that, when administered to a subject, results in a therapeutic benefit.

According to the invention, an effective amount is an amount of at least one compound of Table 1 or FIG. 11, which reduces one or more clinical symptom of one or more of the aforementioned diseases and/or reduces neural damage related to metabolism of APP by BACE1 or inhibit levels of total tau, disease-associated phosphorylated or presence of modified forms of tau. In one example, an effective amount is an amount of at least one compound of Table 1, and/or at least one compound depicted in FIG. 11, that reduces the production of sAPPβ or Aβ generated by the metabolism of APP by BACEI or inhibits levels of total tau, disease-associated phosphorylated or presence of modified forms of tau.

In certain non-limiting embodiments, the effective amount of at least one compound of Table 1, and/or at least one compound depicted in FIG. 11, may be determined via an in vitro assay, for example, as in the Examples sections presented below.

In certain non-limiting embodiments, an effective amount of a compound of Table 1, and/or at least one compound depicted in FIG. 11, may be correlated with the compound's inhibitory characteristic in the in vitro assay compared to a control cell line that was not contacted with the candidate compound, wherein a reduction of the target protein (e.g, Aβ) or phosphorylation (e.g., tau) compared to the control cell line correlates with the compound's therapeutic efficacy.

In certain non-limiting embodiments, an effective amount of a compound of Table 1, and/or at least one compound depicted in FIG. 11—may be correlated with the compound's inhibitory characteristics in the in vitro assay by at least 0.1, or by at least 0.5, or by at least 1, or by at least 1.5, or by at least 2, or by at least 2.5, or by at least 3, or by at least 3.5, or by at least 4, or by at least 4.5, or by at least 5, or by at least 5.5, or by at least 6 or more standard deviations above a control level of detected in the in vitro assay when the compound is tested at a concentration of about 0.2 μM, or about 2 μM, or about 2.2 μM, or about 10 μM, or about 100 AM, our about 1000 μM, wherein such a reduction correlates with a compound's therapeutic efficacy. In one embodiment, the control level of inhibition may be the average level in control cell lines that are not contacted with the candidate compound. In other embodiments, the control level may be the average level of inhibition achieved by a series of compounds tested in the in vitro assay.

In certain, non-limiting embodiments, an effective amount of a compound of Table 1, and/or at least one compound depicted in FIG. 11, may be correlated with the compound's level of inhibition being about 4 standard deviations greater than a control level of inhibition, when the compound is administered at a concentration of 0.2 μM in the in vitro assay.

In certain, non-limiting embodiments, an effective amount of a compound of Table 1, and/or at least one compound depicted in FIG. 11, may be correlated with the compound's level of inhibition being about 4 standard deviations greater than a control level of inhibition, when the compound is administered at a concentration of 2 μM in the in vitro assay.

In certain, non-limiting embodiments, an effective amount of a compound of Table 1, and/or at least one compound depicted in FIG. 11, may be correlated with the compound's level of inhibition being about 4 standard deviations greater than a control level of inhibition, when the compound is administered at a concentration of 10 μM in the in vitro assay.

In certain, non-limiting embodiments, an effective amount of a compound of Table 1, and/or at least one compound depicted in FIG. 11, may be correlated with the compound's level of inhibition being about 4 standard deviations greater than a control level of inhibition, when the compound is administered at a concentration of 100 μM in the in vitro assay.

In certain, non-limiting embodiments, an effective amount of a compound of Table 1, and/or at least one compound depicted in FIG. 11, may be correlated with the compound's level of inhibition being about 4 standard deviations greater than a control level of inhibition, when the compound is administered at a concentration of 1000 μM in the in vitro assay.

In certain, non-limiting embodiments, an effective amount of a compound of Table 1, and/or at least one compound depicted in FIG. 11, may be that amount that inhibits the target (e.g, Aβ) or phosphorylation (e.g., phosphorylation of tau) by at least 5%, by at least 10%, by at least 20%, by at least 30%, by at least 40%, by at least 50%, by at least 60%, by at least 70%, by at least 80%, by at least 90%, or by 100% when compared to the level in a control cell line that was not contacted with the candidate compound, wherein such a reduction correlates with a compound's therapeutic efficacy.

In certain, non-limiting embodiments, an effective amount of a compound of Table 1, and/or at least one compound depicted in FIG. 11, may be that amount which reduces the level of target (e.g, Aβ) or phosphorylation (e.g., phosphorylation of tau) by at least about 50% compared to a control cell line that was not contacted with the candidate compound. Preferably the compound is tested at a concentration ranging from about 1000 μM to about 0.01 μM, from about 100 μM to about 0.01 μM, or from about 10 μM to about 0.01 µM in the in vitro assay, wherein such a reduction at the above-described concentrations is correlative with the compound's therapeutic efficacy.

5.4. Administration of Treatments

According to the invention, the component or components of a pharmaceutical composition of the invention may be administered by, for example and not by way of limitation, intravenous, intra-arterial, intramuscular, intradeinial, transdermal, subcutaneous, oral, intraperitoneal, intraventricular, and intrathecal administration.

In particular non-limiting embodiments, the therapeutic compound can be delivered in a controlled or sustained release system. For example, a compound or composition may be administered using intravenous infusion, an implantable osmotic pump, a transdermal patch, liposomes, or other modes of administration. In one embodiment, a pump may be used (see Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Langer and Wise eds., 1974, Medical Applications of Controlled Release, CRC Press: Boca Raton, Fla.; Smolen and Ball eds., 1984, Controlled Drug Bioavailability, Drug Product Design and Performance, Wiley, N.Y.; Ranger and Peppas, 1983, J. Macromol. Sci. Rev. Macromol. Chem., 23:61; Levy et al., 1985, Science 228:190; During et al., 1989, Ann. Neurol., 25:351; Howard et al., 9189, J. Neurosurg. 71:105). In yet another embodiment, a controlled release system can be placed in proximity of the therapeutic target, i.e., the heart or a blood vessel, thus requiring only a fraction of the systemic dose (see, e.g., Goodson, 1984, in Medical Applications of Controlled Release, supra, Vol. 2, pp. 115-138). Other controlled release systems known in the art may also be used.

5.5. Pharmaceutical Compositions

The compounds and compositions of the invention may be formulated as pharmaceutical compositions by admixture with a pharmaceutically acceptable carrier or excipient.

In certain, non-limiting embodiments, the pharmaceutical compositions of the present invention may comprise an effective amount of at least one compound of Table 1, and/or at least one compound depicted in FIG. 11, and a physiologically acceptable diluent or carrier. The pharmaceutical composition may further comprise a second drug, for example, but not by way of limitation, a compound for the treatment of Alzheimer's disease, such as an acetylcholinesterase inhibitor or an NMDA glutamate receptor antagonist (e.g. memantine).

The phrase "pharmaceutically acceptable" refers to substances that are physiologically tolerable when administered to a subject. Preferably, but not by way of limitation, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, or, for solid dosage forms, may be standard tabletting excipients. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

In certain, non-limiting embodiments, the therapeutic compounds of the present invention can be delivered in a vesicle, in particular a liposome (see Langer, 1990, Science 249:1527-1533; Treat et al., 1989, in Liposomes in the Therapy of Infectious Disease and Cancer, Lopez-Berestein and Fidler eds., Liss: New York, pp. 353-365; Lopez-Berestein, ibid., pp. 317-327; see generally Lopez-Berestein, ibid.).

6. WORKING EXAMPLES

6.1. Example 1

Embryonic Stem Cell Culture.

ES cells were cultured on mitomycin C (Sigma) treated primary mouse embryonic fibroblasts (PMEF) for two passages after thawing, with subsequent PMEF deprivation for two passages in ES medium containing supplemented with 1,000 U/ml LIP (Millipore). Prior to plating, cell culture dishes were coated with 0.1% gelatin (Chemicon) for 30 min. ES medium was changed every day.

Directed Differentiation of ES Cells into Pyramidal Neurons.

Methods were adapted and optimized from Bibel, M., et al. Nat. Neurosci. 7, 1003-9 (2004) and Bibel, M., Richter, J., Lacroix, E., & Barde, Y. A. Nat Protoc. 2, 1034-1043 (2007)). Prior to differentiation, newly defrosted ES cells were cultured on PMEF cells for 2 passages. Cells were subsequently passaged twice without feeder cells on gelatin-coated plates. After 2 feeder-free passages cells could be frozen and used to begin Embyoid Body (EB) formation immediately after thawing. Ernbryoid body formation: Feeder-free ES cells were washed in PBS (Gibco) and trypsinized (0.025% trypsin/0.75 mM EDTA without calcium and magnesium; Chemicon) for 5 min at 37° C. Cells were harvested in EB medium containing DMEM (Millipore Specialty Media); 10% ES grade FBS (Thermo Fisher Scientific Dyclone); non-essential amino acids (Millipore Specialty Media); nucleosides (Millipore Specialty Media); glutamine (Millipore Specialty Media) and β-mercaptoethanol (Gibco) and counted. Cells were plated in EB medium on non-adherent bacterial Petri dishes (Greiner Bio-One) at a concentration of $3\times10^6$ cells/100 mm. Medium was changed every 2 days for 8 days and 5 µM retinoic acid (Sigma) was added to EB medium on days 4 and 6. Plating of neurons: Tissue culture plates and slides were coated with 10 µg/ml poly-D-Lysine (Sigma) in borate buffer (150 mM, pH 8.6) and 3 µg/ml laminin (Sigma). Embroyid bodies were collected in EB medium, washed twice with PBS and trypsinized for 5 min in 37° C. water bath. Trypsinized embryoid bodies were dissociated using a 1 ml pipette tip in EB medium, and the cell suspension was centrifuged at 1,500 rpm at RT for 5 min. The pellet was resuspended in Advanced DMEM/F12 (Gibco) supplemented with N2 (Gibco) and filtered through a 40 µM nylon strainer. Cells were counted using the trypan-blue exclusion method and plated at a density of $1.5\times10^5$ cells/cm$^2$ in 6 well (surface area (SA)/well=10 cm$^2$), 12 well (SA/well=4 cm$^2$), 35 mm (SA/well=4 cm$^2$), 24 well (SA/well=2 cm$^2$), and 96 well (SA/well=0.3 cm$^2$) plates. N2 supplemented medium was changed after 2 and 24 hrs. Media was changed to Neurobasal medium (Gibco) supplemented with B27 (Gibco), glutamine, penicillin and streptomycin at 48 hrs after plating. Subsequently, neuronal media was changed every 2 days. At day 7 after plating, referred to as days in vitro 7 (DIV 7) neuronal medium was supplemented with 25 uM β-mercaptoethanol (Gibco).

Immunocytochemistry.

Neuronal β-Tubulin III was detected by TUJ1 antibody from Covance, MAP-2 antibody was from BD Biosciences, and EMX1 antibody is a pyramidal neuron marker (Chan, C. H., et al., Cereb Cortex. 11, 1191-8 (2001).) and was from Santa Cruz Biotechnology. GFAP and PSD-95 antibodies were from Thermo Scientific and synaptophysin antibody was from Epitomics. At indicated DIV, cells were washed with PBS and fixed with 4% paraformaldehyde (Electron Microscopy Sciences) for 15 min. Cells were permiabilized with 0.1% Triton X-100 (Roche), blocked in normal goat serum (EMD) and incubated with primary antibodies in normal goat serum in PBS with 0.1% (or 0.2% for detection of MAP2B) Triton X-100 overnight at 4° C. Detection was achieved using fluorescent Alexa Fluor secondary antibodies (Invitrogen/Molecular Probes). Confocal images were collected with Nikon C1 digital scanning laser confocal system attached to an Olympus IX71 inverted scope using a 100× objective.

Transmission Electron Microscopy.

Neurons were plated in a 35 mm dish as above and were fixed with 2.5% glutaraldehyde in 0.1M Sorenson's buffer (PH 7.2) for at least one hour. Cells were then postfixed with 1% OsO4 also in Sorenson's buffer for one hour. Enblock staining was performed using 1% tannic acid. After dehydration cells were embedded in a mixture of Lx-112 (Ladd Research Industries, Inc.) and Embed-812 (EMS, Fortwashington, Pa.). Thin sections were cut on the MT-7000 ultramicrotome. The sections were stained with uranyl acetate and lead citrate and examined under a JEOL JEM-1200 EXIT electron microscope. Pictures were taken on an ORCA-HR digital camera (Hamamatsu) and recorded with a AMT Image Capture Engine.

Western Blot Analysis.

Actin antibody was from Sigma; CamKIIa antibody was from BD biosciences; APP (human) was detected using 6e10 from Covance and mouse APP, and CTFs were detected using CT-Maxi (18) The BACE1 antibody was a generous gift from R. Vassar (Northwestern University) and PS1-loop antibody was a generous gift from J. Lah and A. Levey (Emory University). Cells were grown for the indicated DIV and harvested in lysis buffer containing 10 mM Tris-HCl, pH 7.4, 150 mM NaCl, 1% Triton X-100, 0.25% NP-40 and 2 mM EDTA. Lysate was centrifuged at 14,000×g for 15 minutes at 4° C. and the protein concentration of the supernatant was determined using the BCA protein assay (Pierce) and diluted into Laemmli sample buffer with 5% β-mercaptoethanol. Protein was separated on 4-20% Tris/Glycine gels (Invitrogen) using SDS-PAGE and transferred to PVDF membranes for Western blot analysis.

Analysis of APP Processing.

Day 12-30 neurons were infected with a lentivirus carrying the Swedish variant of human APP (pLenti6/hAPPsw). 24 hrs after infection cell medium was changed and 48 hours after infection cells were treated with secretase inhibitors and conditioned media was collected for 24 hrs. The levels of Aβ42 and Aβ40 in conditioned media were determined using sandwich ELISA (Invitrogen) according to the manufacturer's protocol. Total Aβ was detected by immunoprecipitating conditioned medium with 6E10 (Covance) or 7N22 (Invitrogen) antibodies overnight at 4° C. Samples were separated using the NuPAGE gel system and Aβ peptides detected by quantitative Western blotting with 6E10. Full-length APP was detected by Western blot analysis using 6E10 (Covance) or polyclonal antibody against the C-terminus of APP (APP-Ctmaxi) (Okada, H., et al. FASEB J. 24, 2783-94 (2010)). For detection of sAPPβ and sAPPα conditioned medium from DIV12-30 differentiated mouse embryonic stem cell derived neurons was harvested 24 hours after a media change. Immunoprecipitation of sAPPβ was performed using sβsw antibody which was generated by immunizing rabbits with keyhole limpet hemocyanin-conjugated peptides corresponding to the C-terminal region of secreted APPβsw (C)GGGISEVNL. This antibody detects APPsw specifically and does not detect full-length APP. Protein G plus/Protein A agarose suspension (Calbiochem) was used to precipitate the antibody-protein complex. The immunoprecipitate was subjected to SDS-PAGE followed by Western blot detection using 22C11 (Chemicon) or LN27 (Covance). sAPPα was immunoprecipitated with 6e10 and detected on Western blot with LN27.

Cell Viability Assay.

Neurons were grown in a 96 well plate and incubated with Cell Quanti-Blue reagent from Bio Assay Systems which is a resorufin based assay which fluoresces proportionally to the number of live cells. Fluorescence was detected using a Tecan Infinite 200 PRO multimode plate reader after 1-4 hours of incubation with the reagent.

Miniatuization of Aβ Detection from Tg2576 ES Cell Derived Neurons.

Tg2576 ES-derived neurons were plated at $1.5 \times 10^5$ cells/$cm^2$ and at DIV 10 neurons were treated with 10 μM β-secretase 1 inhibitor IV (BACE inh), 20 nM γ-secretase inhibitor, Compound E (CpdE) or 100 μM α-secretase inhibitor (TAPI-2) for 24 hours. Media was then collected and subjected to Aβ40 and Aβ42 detection using human specific ELISA (Invitrogen). Data were analyzed using Graph Pad Prism software to fit log (agonist) vs response curves.

Generation of ES Cell Transfectants Stably Expressing Human PS1 Mutants.

To generate a stable line of ES cells expressing PS1 wild-type and FAD variants, for each vector, $3 \times 10^6$ ES cells were resuspended in Nucleofector solution (Amaxa Neucleofector, Lonza) and mixed with 20 μg plasmid carrying human wild-type or FAD mutant PS1 and neomycin selection marker in the pcDNA3.1 vector. Cells were electroporated using program A-13 (Amaxa), resuspended in 6 ml ES medium and plated onto a 60 mm cell culture dish containing feeder cells. Selection with G418 (250-500 μg/ml) was started 24 hours after electroporation.

FM 4-64 Staining.

After 18-21 days in culture neurons were labeled by electrical stimulation with 600 stimulations at 10 Hz in the presence of the fluorescent styryl membrane probe FM 4-64 (Molecular Probes) at a concentration of 10 mM followed by washing in normal saline solution for 10 min (Gitler, D., Cheng, Q., Greengard, P., & Augustine, G. J. J Neurosci. 28, 10835-43 (2008)). The internalized dye was released by 1000 stimulations at 10 Hz. The images were taken using a 60× objective mounted on an Olympus X81 epifluoresent microscope before and after the second stimulation.

Aβ Oligomer Preparation.

Aβ oligomer prepared as previously described (Dahlgren, K. N. et al. J Biol Chem. 277, 32046-53 (2002) and Stine, W. B. Jr., Dahlgren, K. N., Krafft, G. A., & LaDu, M. J. J Biol Chem. 278, 11612-22 (2003)) for 24 hours. Briefly, oligomer was diluted in HPIF and allowed to air dry followed by speed-vac concentration to from a film. The film was resuspended in DMSO at 1 mM and stored at −20 C until use or a maximum of 2 weeks. DMSO stock was diluted to 0.1 mM in cold PBS and incubated overnight for an oligomeric enriched Aβ preparation.

Aβ Oligomer Induced Changes in Synaptic Proteins and Spine Density.

After 21 days in culture (DIV 21) neurons were treated with 200 nM Aβ oligomer for 24 hours. Neurons were fixed using 4% paraformaldehyde, 4% sucrose in PBS for 20 minutes. For quantification of PSD-95 and synaptophysin (Okabe, S., Miwa, A., & Okado, H. J Neurosci. 21, 6105-14 (2001)), neurons were stained with antibodies against these proteins and detected with Alexa tagged secondary antibodies (Molecular Probes). For spine analysis, after fixation, neurons were labeled with a lipophilic dye that integrates readily into membranes, DiI, (Molecular Probes; Moolman, D. L., Vitolo, O. V., Vonsattel, J. P., Shelanski, M. L. J Neurocytol. 33, 377-87 (2004), and Smith, D. L., Pozueta, J., Gong, B., Arancio, O., & Shelanski, M. Proc Natl Acad Sci USA 106, 16877-82 (2009)). Tungston particles were coated with DiI and propelled into cells using a Gene Gun (Biorad). Dye was allowed to diffuse over-night by incubating cells in PBS at 4° C. before cells were mounted using VectaShield mounting media (Vector). Images were collected on an inverted Olympus microscope with a 100× objective using a Nikon C2 confocal laser microscope system. For spine analysis, a series of z-seetions was taken at 0.5 μM at 3× zoom. Images were stacked and used for a 2-D projection using ImageJ 1.4 g software (NIH). For particle analysis, the RGB colors were split, threshold was set for each image, and the analyze particles tool was selected. Spines and dendrites were measured with the segmented line tool in ImageJ.

Phospho-CREB Detection.

Neurons were grown to maturity and pre-treated for 1 hour in the presence or absence of Aβ oligomer preparation. Subsequently cultures were treated 10 minutes under stimulating conditions (150 mM, 5 mM KCl, 2 mM CaCl2, 30 mM glucose, 10 mM HEPES, 10 μM NMDA) or non-stimulating conditions (120 mM NaCl, 3 mM KCl, 2 mM CaC12, 2 mM MgCl2, 15 mM glucose, 15 mM HEPES pH 7.4) in the presence or absence of Aβ oligomer preparation (Vitolo O V, et al. Proc Natl Acad Sci USA 99, 13217-21 (2002) and Snyder, E. M., et al. Nat Neurosci. 8, 1051-8 (2005)). Protein was solubilized immediately in Laemmli sample buffer and loaded (v/v) to 4-20% Tris/Glycine gel (Invitrogen). Protein was separated using SDS-PAGE and quantitative Western blotting was accomplished using the infra-red secondary antibodies (Rockland) detection with the Licor Odyssey Infrared Imager with solid-state diode laser at 685 nm and 785 nm. Total CREB primary antibody was from Santa Cruz Biotechnology and phospho-CREB (S133) primary antibody was from Invitogen.

6.2. Example 2

Mouse ES cells isolated from. Tg2576 mice were subjected to directed differentiation as previously described. After dissociation of embryoid bodies, neurons were plated in poly-D-lysine and laminin coated 96 well black plates at a density of 1.5×105 cells/cm2 which is 45,000 cells/well. Media was changed to N2 containing media after 4 hours and again the next day after plating. Two days after plating, media was changed to B27 containing media which was replaced every 2 days after that. On day 8 after plating the mouse ES derived neurons were treated with the compounds from a library of 446 clinically relevant compounds which have a history of use in human clinical trials, the NIH clinical collection (NCC) (http://www.nihclinicalcollection.com/), for 24 hours in 150 μl B27 media. Each plate of ES derived neurons was treated with NCC compounds, DMSO (negative control), and the positive controls for Aβ reduction BACE inhibitor IV (Calbiochem) and Compound E. After 24 hours, 100 μl conditioned media was removed and frozen at −80° C. until further analysis for Aβ40 content. The remaining cells in 50 μl media were subjected to cell viability assay CellQuanti Blue (BioAssay Systems). Conditioned media was subjected to Aβ40 quantification using Aβ40 ELISA (Invitrogen). Compounds which lowered Aβ40 levels in the conditioned media were identified as hits if they reduced Aβ40 by 4 standard deviations of the negative control (DMSO) but maintained cell viability. Cell viability was defined by CellQuanti Blue fluorescent signal maintained within two standard deviations of fluorescent signal from the control treated (DMSO) cells. High potency hits were defined by reducing Aβ40 40% or more (signal 60% of DMSO control).

Results for FIG. 10 and Table 1.

Hits were defined as lowering Aβ by 4 standard deviations below the negative control (DMSO) treated condition but maintaining cell viability within 2 standard deviations of control. This resulted in 36 hits which is a hit rate of 8.1% (Table 1, in section 5.2, above). High potency hits were defined by ability to lower Aβ40 40% or more, resulting in 10 high potency hits. Three high priority hits were confirmed from independent compound sources and subjected to further characterization such as IC50 determination: phenelzine, 2.5 μM; icariin, 5.1 μM and amiridine, 2.3 μM.

6.3. Example 3

Assay for Tau

Wild type, mouse embryoinc stem cells were differentiated into pyramidal neurons using the protocol described in Example 1. ES cell-derived neurons were treated at 14 DIV for 48 hr with either vehicle (D, DMSO) or various histone demethylase inhibitors (inhibitor compounds 1-10). Tau isoforms were detected by Western blot analysis of the cell lysates using the indicated antibodies, See FIG. 11. CP13 recognizes tau phosphorylation at ser202/205. PHF recognizes tau phosphorylation at ser396/404. TUJ1 (Neuron-specific class III beta-tubulin) is used as a loading control.

List of inhibitor compounds tested for their ability to inhibit levels of total tau, disease-associated phosphorylated or presence of modified forms of tau include (asterisk denotes hit compounds): *1. pargyline (LSD1 inhibitor)—1000 uM; *2. deprenyl (LSD1 inhibitor)—1000 uM; *3. propargyl (LSD1 inhibitor)—100 uM; 4. phenelzine (LSD1 inhibitor)—100 uM; 5. tranylcyprmine (LSD1 inhibitor)—200 uM; *6. S2101 (LSD1 Inhibitor II, EMD Biosciences catalog #489477)—LSD1 inhibitor—1 uM; 7. N-oxyalyl-glycine (NOG) (JMJD2s inhibitor)—1000 uM; *8. pyradine (JMJ2A and E inhibitor)—1000 uM; *9. disulfiram (JMJ2A inhibitor)—20 uM; *10. ebselen (JMJ2A inhibitor)—20 uM.

Various publications are cited herein, the contents of which are hereby incorporated by reference in their entireties.

What is claimed is:

1. A method of reducing levels of total tau comprising administration of S2101.

2. A method of reducing levels of phosphorylated forms of tau comprising administration of S2101.

* * * * *

UNITED STATES PATENT AND TRADEMARK OFFICE
CERTIFICATE OF CORRECTION

PATENT NO. : 9,696,306 B2
APPLICATION NO. : 14/020776
DATED : July 4, 2017
INVENTOR(S) : Tae-Wan Kim et al.

Page 1 of 1

It is certified that error appears in the above-identified patent and that said Letters Patent is hereby corrected as shown below:

In the Specification

Column 1, Line 13, "The subject matter of this application was developed at least in part using National Institutes of Health Grant Nos. NS051186 and AG033199, so that the United States Government holds certain rights herein." should read -- This invention was made with government support under grants NS051186 and AG033199 awarded by the National Institutes of Health. The Government has certain rights in this invention. --

Signed and Sealed this
Seventh Day of November, 2017

Joseph Matal
*Performing the Functions and Duties of the
Under Secretary of Commerce for Intellectual Property and
Director of the United States Patent and Trademark Office*